(12) United States Patent
Liu et al.

(10) Patent No.: US 7,842,041 B2
(45) Date of Patent: Nov. 30, 2010

(54) STEERABLE VERTEBROPLASTY SYSTEM

(75) Inventors: Y. King Liu, Petaluma, CA (US); Jan R. Lau, Windsor, CA (US); Judson E. Threlkeld, Camas, WA (US); Michael T Lyster, Riverwoods, IL (US)

(73) Assignee: Osseon Therapeutics, Inc., Santa Rosa, CA (US)

( * ) Notice: Subject to any disclaimer, the term of this patent is extended or adjusted under 35 U.S.C. 154(b) by 0 days.

(21) Appl. No.: 12/261,987

(22) Filed: Oct. 30, 2008

(65) Prior Publication Data

US 2009/0131948 A1 May 21, 2009

Related U.S. Application Data

(62) Division of application No. 11/941,764, filed on Nov. 16, 2007.

(51) Int. Cl.
- *A61B 17/58* (2006.01)
- *A61B 17/60* (2006.01)
- *A61F 2/00* (2006.01)
- *A61M 29/00* (2006.01)

(52) U.S. Cl. .................................. 606/94; 604/95.04

(58) Field of Classification Search ............. 604/95.01, 604/95.04, 524, 528; 606/92–95
See application file for complete search history.

(56) References Cited

U.S. PATENT DOCUMENTS

| | | | |
|---|---|---|---|
| 3,625,200 A | 12/1971 | Muller | |
| 3,908,637 A | 9/1975 | Doroshow | |
| 4,033,331 A | 7/1977 | Guss et al. | |
| 4,131,597 A | 12/1978 | Bluethgen et al. | |
| 4,236,520 A | 12/1980 | Anderson | |
| 4,276,880 A | 7/1981 | Malmin | |
| 4,294,251 A | 10/1981 | Greenwald et al. | |
| 4,337,773 A | 7/1982 | Raftopoulos et al. | |
| 4,399,814 A | 8/1983 | Pratt, Jr. et al. | |
| 4,578,061 A | 3/1986 | Lemelson | |
| 4,627,434 A | 12/1986 | Murray | |
| 4,653,489 A | 3/1987 | Tronzo | |
| 4,668,295 A | 5/1987 | Bajpai | |
| 4,722,948 A | 2/1988 | Sanderson | |
| 4,731,054 A | 3/1988 | Billeter et al. | |
| 4,747,840 A | 5/1988 | Ladika et al. | |
| 4,748,969 A | 6/1988 | Wardle | |
| 4,784,638 A | 11/1988 | Ghajar et al. | |
| 4,842,603 A | 6/1989 | Draenert | |
| 4,843,112 A | 6/1989 | Gerhart et al. | |
| 4,846,814 A | 7/1989 | Ruiz | |

(Continued)

OTHER PUBLICATIONS

U.S. Appl. No. 12/469,611, filed May 20, 2009, Lau et al.

(Continued)

*Primary Examiner*—Nicholas D Lucchesi
*Assistant Examiner*—Nathan R Price
(74) *Attorney, Agent, or Firm*—Knobbe, Martens, Olson & Bear LLP

(57) ABSTRACT

Methods and devices for augmenting bone, such as in performing vertebroplasty are disclosed. A bone cement injection needle is provided, having a laterally deflectable distal end. Systems are also disclosed, including the steerable injection needle, introducer and stylet. The system may additionally include a cement delivery gun, one-time use disposable cement cartridges and a cement mixing chamber. Methods are also disclosed.

13 Claims, 20 Drawing Sheets

U.S. PATENT DOCUMENTS

| | | |
|---|---|---|
| 4,865,586 A | 9/1989 | Hedberg |
| 4,869,906 A | 9/1989 | Dingeldein et al. |
| 4,888,366 A | 12/1989 | Chu |
| 4,900,303 A | 2/1990 | Lemelson |
| 4,961,731 A | 10/1990 | Bodicky et al. |
| 4,963,151 A | 10/1990 | Ducheyne et al. |
| 4,969,870 A | 11/1990 | Kramer et al. |
| 4,969,888 A | 11/1990 | Scholten et al. |
| 4,982,730 A | 1/1991 | Lewis, Jr. |
| 5,004,501 A | 4/1991 | Faccioli |
| 5,017,627 A | 5/1991 | Bonfield |
| 5,029,558 A | 7/1991 | O'Leary et al. |
| 5,049,137 A | 9/1991 | Thompson |
| 5,049,157 A | 9/1991 | Mittelmeier et al. |
| 5,059,193 A | 10/1991 | Kuslich |
| 5,085,861 A | 2/1992 | Gerhart et al. |
| 5,088,991 A | 2/1992 | Weldon |
| 5,092,891 A | 3/1992 | Kummer et al. |
| 5,108,404 A | 4/1992 | Reiley et al. |
| 5,112,303 A | 5/1992 | Pudenz et al. |
| 5,147,334 A | 9/1992 | Moss |
| 5,156,606 A | 10/1992 | Chin |
| 5,163,431 A | 11/1992 | Griep |
| 5,184,757 A | 2/1993 | Giannuzzi |
| 5,188,619 A | 2/1993 | Myers |
| 5,196,201 A | 3/1993 | Larsson et al. |
| 5,197,971 A | 3/1993 | Bonutti |
| 5,211,631 A | 5/1993 | Sheaff |
| 5,242,082 A | 9/1993 | Giannuzzi |
| 5,264,214 A | 11/1993 | Rhee et al. |
| 5,266,248 A | 11/1993 | Ohtsuka et al. |
| 5,269,750 A | 12/1993 | Grulke et al. |
| 5,285,795 A * | 2/1994 | Ryan et al. ................ 600/563 |
| 5,295,980 A | 3/1994 | Ersek |
| 5,296,026 A | 3/1994 | Monroe et al. |
| 5,308,342 A | 5/1994 | Sepetka et al. |
| 5,336,699 A | 8/1994 | Cooke et al. |
| 5,343,877 A | 9/1994 | Park |
| 5,352,715 A | 10/1994 | Wallace et al. |
| 5,356,629 A | 10/1994 | Sander |
| 5,360,416 A | 11/1994 | Ausherman et al. |
| 5,368,598 A | 11/1994 | Hasson |
| 5,372,587 A | 12/1994 | Hammerslag et al. |
| 5,378,234 A | 1/1995 | Hammerslag et al. |
| 5,380,307 A | 1/1995 | Chee et al. |
| 5,385,563 A | 1/1995 | Gross |
| 5,389,073 A | 2/1995 | Imran |
| 5,425,770 A | 6/1995 | Piez et al. |
| 5,431,168 A | 7/1995 | Webster, Jr. |
| 5,431,639 A | 7/1995 | Shaw |
| 5,480,382 A | 1/1996 | Hammerslag et al. |
| 5,484,424 A | 1/1996 | Cottenceau et al. |
| 5,489,275 A | 2/1996 | Thompson et al. |
| 5,496,330 A | 3/1996 | Bates et al. |
| 5,512,610 A | 4/1996 | Lin |
| 5,514,137 A | 5/1996 | Coutts |
| 5,531,715 A | 7/1996 | Engelson et al. |
| 5,533,985 A | 7/1996 | Wang |
| 5,535,922 A | 7/1996 | Maziarz |
| 5,549,542 A | 8/1996 | Kovalcheck |
| 5,549,679 A | 8/1996 | Kuslich |
| 5,554,114 A | 9/1996 | Wallace et al. |
| 5,571,085 A | 11/1996 | Accisano, III |
| 5,574,075 A | 11/1996 | Draenert |
| 5,616,121 A | 4/1997 | McKay |
| 5,624,396 A | 4/1997 | McNamara et al. |
| 5,637,091 A | 6/1997 | Hakky et al. |
| 5,681,289 A | 10/1997 | Wilcox et al. |
| 5,681,317 A | 10/1997 | Caldarise |
| 5,685,826 A | 11/1997 | Bonutti |
| 5,709,697 A | 1/1998 | Ratcliff et al. |
| 5,725,568 A | 3/1998 | Hastings |
| 5,735,829 A | 4/1998 | Cherian |
| 5,741,320 A | 4/1998 | Thornton et al. |
| 5,800,408 A | 9/1998 | Strauss et al. |
| 5,810,867 A | 9/1998 | Zarbatany et al. |
| 5,820,592 A | 10/1998 | Hammerslag |
| 5,847,046 A | 12/1998 | Jiang et al. |
| 5,858,003 A | 1/1999 | Atala |
| 5,860,952 A | 1/1999 | Quinn |
| 5,876,373 A | 3/1999 | Giba et al. |
| 5,902,839 A | 5/1999 | Lautenschlager |
| 5,914,356 A | 6/1999 | Erbe |
| 5,928,239 A | 7/1999 | Mirza |
| 5,931,829 A | 8/1999 | Burbank et al. |
| 5,972,015 A | 10/1999 | Scribner et al. |
| 5,997,581 A | 12/1999 | Khalili |
| 6,019,765 A | 2/2000 | Thornhill et al. |
| 6,027,487 A | 2/2000 | Crocker |
| 6,030,360 A | 2/2000 | Biggs |
| 6,059,739 A | 5/2000 | Baumann |
| 6,066,154 A | 5/2000 | Reiley et al. |
| 6,066,176 A | 5/2000 | Oshida |
| 6,080,801 A | 6/2000 | Draenert |
| 6,099,514 A | 8/2000 | Sharkey et al. |
| 6,110,155 A | 8/2000 | Baudino |
| 6,127,597 A | 10/2000 | Beyar et al. |
| 6,146,355 A | 11/2000 | Biggs |
| 6,183,435 B1 | 2/2001 | Bumbalough et al. |
| 6,203,507 B1 | 3/2001 | Wadsworth et al. |
| 6,203,574 B1 | 3/2001 | Kawamura |
| 6,228,052 B1 | 5/2001 | Pohndorf |
| 6,228,904 B1 | 5/2001 | Yadav |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,251,092 B1 | 6/2001 | Qin et al. |
| 6,280,413 B1 | 8/2001 | Clark et al. |
| 6,280,434 B1 | 8/2001 | Kinoshita et al. |
| 6,280,456 B1 | 8/2001 | Scribner et al. |
| 6,280,473 B1 | 8/2001 | Lemperle et al. |
| 6,291,547 B1 | 9/2001 | Lyles |
| 6,332,894 B1 | 12/2001 | Stalcup |
| 6,358,251 B1 | 3/2002 | Mirza |
| 6,383,188 B2 | 5/2002 | Kuslich et al. |
| 6,437,019 B1 | 8/2002 | Rusin |
| 6,440,138 B1 | 8/2002 | Reiley et al. |
| 6,447,514 B1 | 9/2002 | Stalcup et al. |
| 6,479,565 B1 | 11/2002 | Stanley |
| 6,484,904 B1 | 11/2002 | Horner et al. |
| 6,506,217 B1 | 1/2003 | Arnett |
| 6,511,471 B2 | 1/2003 | Rosenman et al. |
| 6,524,296 B1 | 2/2003 | Beals |
| 6,565,588 B1 | 5/2003 | Clement et al. |
| 6,575,978 B2 | 6/2003 | Peterson et al. |
| 6,576,249 B1 | 6/2003 | Gendler et al. |
| 6,592,559 B1 | 7/2003 | Pakter et al. |
| 6,599,961 B1 | 7/2003 | Pienkowski et al. |
| 6,620,162 B2 | 9/2003 | Kuslich et al. |
| 6,623,448 B2 | 9/2003 | Slater |
| 6,638,268 B2 | 10/2003 | Niazi |
| 6,663,647 B2 | 12/2003 | Reiley et al. |
| 6,676,665 B2 | 1/2004 | Foley et al. |
| 6,679,886 B2 | 1/2004 | Weikel et al. |
| 6,689,823 B1 | 2/2004 | Bellare et al. |
| 6,692,532 B1 | 2/2004 | Healy et al. |
| 6,719,761 B1 | 4/2004 | Reiley et al. |
| 6,719,773 B1 | 4/2004 | Boucher et al. |
| 6,743,239 B1 | 6/2004 | Kuehn et al. |
| 6,746,451 B2 | 6/2004 | Middleton et al. |
| 6,752,863 B2 | 6/2004 | Lyles et al. |
| 6,753,007 B2 | 6/2004 | Haggard et al. |
| 6,770,079 B2 | 8/2004 | Bhatnagar et al. |
| 6,814,734 B2 | 11/2004 | Chappuis et al. |

| | | |
|---|---|---|
| 6,814,736 B2 | 11/2004 | Reiley et al. |
| 6,818,001 B2 | 11/2004 | Wulfman et al. |
| 6,832,984 B2 | 12/2004 | Stelzer et al. |
| 6,835,193 B2 | 12/2004 | Epstein et al. |
| 6,837,867 B2 | 1/2005 | Kortelling |
| 6,863,672 B2 | 3/2005 | Reiley et al. |
| 6,869,445 B1 | 3/2005 | Johnson |
| 6,875,219 B2 | 4/2005 | Arramon |
| 6,899,715 B1 | 5/2005 | Beaty |
| 6,899,719 B2 | 5/2005 | Reiley et al. |
| 6,913,594 B2 | 7/2005 | Coleman et al. |
| 6,916,306 B1 | 7/2005 | Jenkins et al. |
| 6,923,813 B2 | 8/2005 | Phillips et al. |
| 6,945,956 B2 | 9/2005 | Waldhauser et al. |
| 6,953,594 B2 | 10/2005 | Lee et al. |
| 6,955,716 B2 | 10/2005 | Xu et al. |
| 6,976,987 B2 | 12/2005 | Flores |
| 6,979,312 B2 | 12/2005 | Shimada |
| 6,979,352 B2 | 12/2005 | Reynolds |
| 6,981,981 B2 | 1/2006 | Reiley et al. |
| 6,991,616 B2 | 1/2006 | Bencini et al. |
| 6,998,128 B2 | 2/2006 | Haggard et al. |
| 7,004,945 B2 | 2/2006 | Boyd et al. |
| 7,008,433 B2 | 3/2006 | Voellmicke et al. |
| 7,018,460 B2 | 3/2006 | Xu et al. |
| 7,029,468 B2 | 4/2006 | Honebrink |
| 7,044,954 B2 | 5/2006 | Reiley et al. |
| 7,059,330 B1 | 6/2006 | Makower et al. |
| 7,063,682 B1 | 6/2006 | Whayne et al. |
| 7,066,942 B2 | 6/2006 | Treace |
| RE92,196 | 7/2006 | Ying et al. |
| 7,081,122 B1 | 7/2006 | Reiley et al. |
| 7,081,161 B2 | 7/2006 | Genge et al. |
| 7,091,258 B2 | 8/2006 | Neubert et al. |
| 7,091,260 B2 | 8/2006 | Kühn |
| 7,094,202 B2 | 8/2006 | Nobis et al. |
| 7,094,286 B2 | 8/2006 | Liu |
| 7,109,254 B2 | 9/2006 | Müller et al. |
| 7,112,205 B2 | 9/2006 | Carrison |
| 7,114,501 B2 | 10/2006 | Johnson et al. |
| 7,138,442 B2 | 11/2006 | Smith |
| 7,153,306 B2 | 12/2006 | Ralph et al. |
| 7,153,307 B2 | 12/2006 | Scribner et al. |
| 7,166,121 B2 | 1/2007 | Reiley et al. |
| 7,172,629 B2 | 2/2007 | McKay |
| 7,186,761 B2 | 3/2007 | Soffiati |
| 7,226,481 B2 | 6/2007 | Kuslich |
| 7,465,318 B2 | 12/2008 | Sennett |
| 2001/0011174 A1 | 8/2001 | Reiley et al. |
| 2001/0023349 A1* | 9/2001 | VanTassel et al. ............. 606/53 |
| 2002/0013600 A1 | 1/2002 | Scribner et al. |
| 2002/0026195 A1 | 2/2002 | Layne et al. |
| 2002/0068974 A1 | 6/2002 | Kuslich et al. |
| 2002/0077595 A1 | 6/2002 | Hundertmark et al. |
| 2002/0082605 A1 | 6/2002 | Reiley et al. |
| 2002/0115742 A1 | 8/2002 | Trieu et al. |
| 2002/0156483 A1 | 10/2002 | Voellmicke et al. |
| 2002/0188299 A1 | 12/2002 | Reiley et al. |
| 2003/0032929 A1* | 2/2003 | McGuckin, Jr. ............. 604/272 |
| 2003/0043963 A1 | 3/2003 | Yamagami et al. |
| 2003/0050644 A1 | 3/2003 | Boucher et al. |
| 2003/0073979 A1 | 4/2003 | Naimark et al. |
| 2003/0130664 A1 | 7/2003 | Boucher et al. |
| 2003/0191489 A1 | 10/2003 | Reiley et al. |
| 2003/0195547 A1 | 10/2003 | Scribner et al. |
| 2003/0220414 A1 | 11/2003 | Axen et al. |
| 2003/0225432 A1 | 12/2003 | Baptiste et al. |
| 2003/0233096 A1 | 12/2003 | Osorio et al. |
| 2004/0023784 A1 | 2/2004 | Yu et al. |
| 2004/0024081 A1 | 2/2004 | Trieu et al. |
| 2004/0024409 A1 | 2/2004 | Sand et al. |
| 2004/0024410 A1 | 2/2004 | Olson et al. |
| 2004/0034384 A1 | 2/2004 | Fukaya |
| 2004/0044350 A1 | 3/2004 | Martin et al. |
| 2004/0087994 A1 | 5/2004 | Suddaby |
| 2004/0092946 A1 | 5/2004 | Bagga et al. |
| 2004/0097612 A1 | 5/2004 | Rosenberg et al. |
| 2004/0127987 A1 | 7/2004 | Evans et al. |
| 2004/0138758 A1 | 7/2004 | Evans et al. |
| 2004/0153064 A1 | 8/2004 | Foley et al. |
| 2004/0153115 A1 | 8/2004 | Reiley et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0210231 A1 | 10/2004 | Boucher et al. |
| 2004/0215343 A1 | 10/2004 | Hochschuler et al. |
| 2004/0220680 A1 | 11/2004 | Yamamoto et al. |
| 2004/0225296 A1 | 11/2004 | Reiss et al. |
| 2004/0226479 A1 | 11/2004 | Lyles et al. |
| 2004/0230309 A1 | 11/2004 | DiMauro et al. |
| 2004/0236186 A1 | 11/2004 | Chu |
| 2004/0247644 A1 | 12/2004 | Bratt et al. |
| 2004/0267271 A9 | 12/2004 | Scribner et al. |
| 2005/0027245 A1 | 2/2005 | Sachdeva et al. |
| 2005/0033303 A1 | 2/2005 | Chappuis et al. |
| 2005/0038383 A1 | 2/2005 | Kelley et al. |
| 2005/0043737 A1 | 2/2005 | Reiley et al. |
| 2005/0060030 A1 | 3/2005 | Lashinski et al. |
| 2005/0070844 A1 | 3/2005 | Chow et al. |
| 2005/0070912 A1 | 3/2005 | Voellmicke |
| 2005/0090852 A1 | 4/2005 | Layne et al. |
| 2005/0113836 A1 | 5/2005 | Lozier et al. |
| 2005/0124989 A1 | 6/2005 | Suddaby |
| 2005/0143827 A1 | 6/2005 | Globerman et al. |
| 2005/0182412 A1 | 8/2005 | Johnson et al. |
| 2005/0182413 A1 | 8/2005 | Johnson et al. |
| 2005/0187556 A1 | 8/2005 | Stack et al. |
| 2005/0199156 A1 | 9/2005 | Khairoun et al. |
| 2005/0209557 A1 | 9/2005 | Carroll et al. |
| 2005/0216018 A1 | 9/2005 | Sennett |
| 2005/0228391 A1 | 10/2005 | Levy et al. |
| 2005/0234425 A1 | 10/2005 | Miller et al. |
| 2005/0240193 A1 | 10/2005 | Layne et al. |
| 2005/0251266 A1 | 11/2005 | Maspero et al. |
| 2005/0251267 A1 | 11/2005 | Winterbottom et al. |
| 2005/0261683 A1 | 11/2005 | Veldhuizen et al. |
| 2006/0024348 A1 | 2/2006 | Engqvist et al. |
| 2006/0041033 A1 | 2/2006 | Bisig |
| 2006/0052743 A1 | 3/2006 | Reynolds |
| 2006/0064101 A1 | 3/2006 | Arramon |
| 2006/0074433 A1 | 4/2006 | McGill et al. |
| 2006/0100635 A1 | 5/2006 | Reiley et al. |
| 2006/0100706 A1 | 5/2006 | Shadduck et al. |
| 2006/0106392 A1 | 5/2006 | Embry |
| 2006/0106459 A1 | 5/2006 | Truckai |
| 2006/0116689 A1 | 6/2006 | Albans et al. |
| 2006/0142732 A1 | 6/2006 | Karmarkar et al. |
| 2006/0149268 A1 | 7/2006 | Truckai et al. |
| 2006/0149281 A1 | 7/2006 | Reiley et al. |
| 2006/0156959 A1 | 7/2006 | Engqvist |
| 2006/0184106 A1 | 8/2006 | McDaniel et al. |
| 2006/0184192 A1 | 8/2006 | Markworth et al. |
| 2006/0206116 A1* | 9/2006 | Yeung ..................... 606/80 |
| 2006/0206136 A1 | 9/2006 | Sachdeva et al. |
| 2006/0217736 A1 | 9/2006 | Kaneko |
| 2006/0229625 A1 | 10/2006 | Truckai et al. |
| 2006/0229631 A1 | 10/2006 | Reiley et al. |
| 2006/0235417 A1 | 10/2006 | Sala |
| 2006/0264945 A1 | 11/2006 | Edidin et al. |
| 2006/0266372 A1 | 11/2006 | Miller et al. |
| 2006/0270750 A1 | 11/2006 | Almen |
| 2006/0271061 A1 | 11/2006 | Beyar et al. |
| 2006/0276797 A1 | 12/2006 | Botimer |
| 2006/0276819 A1 | 12/2006 | Osorio et al. |
| 2006/0293687 A1 | 12/2006 | Bogert |
| 2007/0010845 A1 | 1/2007 | Gong et al. |

| | | | |
|---|---|---|---|
| 2007/0016130 A1 | 1/2007 | Leeflang et al. | |
| 2007/0016211 A1 | 1/2007 | Botimer | |
| 2007/0021769 A1 | 1/2007 | Scribner et al. | |
| 2007/0043373 A1 | 2/2007 | Sala et al. | |
| 2007/0055201 A1 | 3/2007 | Seto et al. | |
| 2007/0055266 A1 | 3/2007 | Osorio et al. | |
| 2007/0055275 A1 | 3/2007 | Schaller | |
| 2007/0055277 A1 | 3/2007 | Osorio et al. | |
| 2007/0055278 A1 | 3/2007 | Osorio et al. | |
| 2007/0055279 A1* | 3/2007 | Sand et al. | 606/92 |
| 2007/0055283 A1 | 3/2007 | Scribner | |
| 2007/0055284 A1 | 3/2007 | Osorio | |
| 2007/0055285 A1 | 3/2007 | Osorio et al. | |
| 2007/0055300 A1 | 3/2007 | Osorio et al. | |
| 2007/0055382 A1 | 3/2007 | Osorio et al. | |
| 2007/0059281 A1 | 3/2007 | Moseley et al. | |
| 2007/0067034 A1 | 3/2007 | Chirico et al. | |
| 2007/0114248 A1 | 5/2007 | Kovac | |
| 2007/0118142 A1 | 5/2007 | Krueger et al. | |
| 2007/0162042 A1 | 7/2007 | Dunker | |
| 2007/0173939 A1 | 7/2007 | Kim et al. | |
| 2007/0185231 A1* | 8/2007 | Liu et al. | 523/116 |
| 2007/0197935 A1 | 8/2007 | Reiley | |
| 2007/0211563 A1 | 9/2007 | DeVries | |
| 2007/0233146 A1 | 10/2007 | Henniges et al. | |
| 2007/0260223 A1 | 11/2007 | Scheibe et al. | |
| 2007/0270876 A1 | 11/2007 | Kuo et al. | |
| 2008/0058840 A1 | 3/2008 | Albrecht | |
| 2008/0195112 A1 | 8/2008 | Liu et al. | |
| 2008/0249481 A1 | 10/2008 | Crainich et al. | |
| 2009/0131867 A1 | 5/2009 | Liu et al. | |
| 2009/0131886 A1 | 5/2009 | Liu et al. | |
| 2009/0131945 A1 | 5/2009 | Liu et al. | |
| 2009/0131950 A1 | 5/2009 | Liu et al. | |
| 2009/0182427 A1 | 7/2009 | Liu et al. | |

OTHER PUBLICATIONS

U.S. Appl. No. 12/469,654, filed May 20, 2009, Lau et al.
U.S. Appl. No. 12/582,597, filed Oct. 2, 2009, Liu et al.
International Search Report for PCT/US08/83698 dated Jan. 22, 2009.
"Confidence Cement System". [Online] Available http://www.disc-o-tech.com/Articles/Article.asp?CategoryID=4&ArticleID=168, accessed Dec. 3, 2007.
Dai et al., "Bone-Particle-Impregnated Bone Cement: An in vivo weight-bearing study," *Journal of Biomedical Materials Research*, vol. 25, 141-156 (1991).
Hasenwinkel et al., "A Novel High-Viscosity, Two-Solution Acrylic Bone Cement: Effect of Chemical Composition on Properties," J. Biomed Mater. Res, vol. 47, No. 1, 36-45 (1999).
Klawitter, J.J. and Hulbert, S.F., "Application of Porous Ceramics for the Attachment of Load Bearing Internal Orthopedic Applications," *J. Biomed. Mater. Res. Symp.*, 2(1), 161-229 (1972).
Liu et al., "Bone-Particle-Impregnated Bone Cement: An In Vitro Study," *Journal of Biomedical Materials Research*, vol. 21, 247-261 (1987).
Park et al., "The Material Properties of Bone-Particle Impregnated PMMA," *Journal of Biomechanical Engineering*, vol. 108, 141-148 (1986).
Park, J.B. and Lakes, S., "Biomaterials: An Introduction—Second Edition," Plenum Press, pp. 177-178 (1992).
US 7,063,700, 06/2006, Michelson (withdrawn)

* cited by examiner

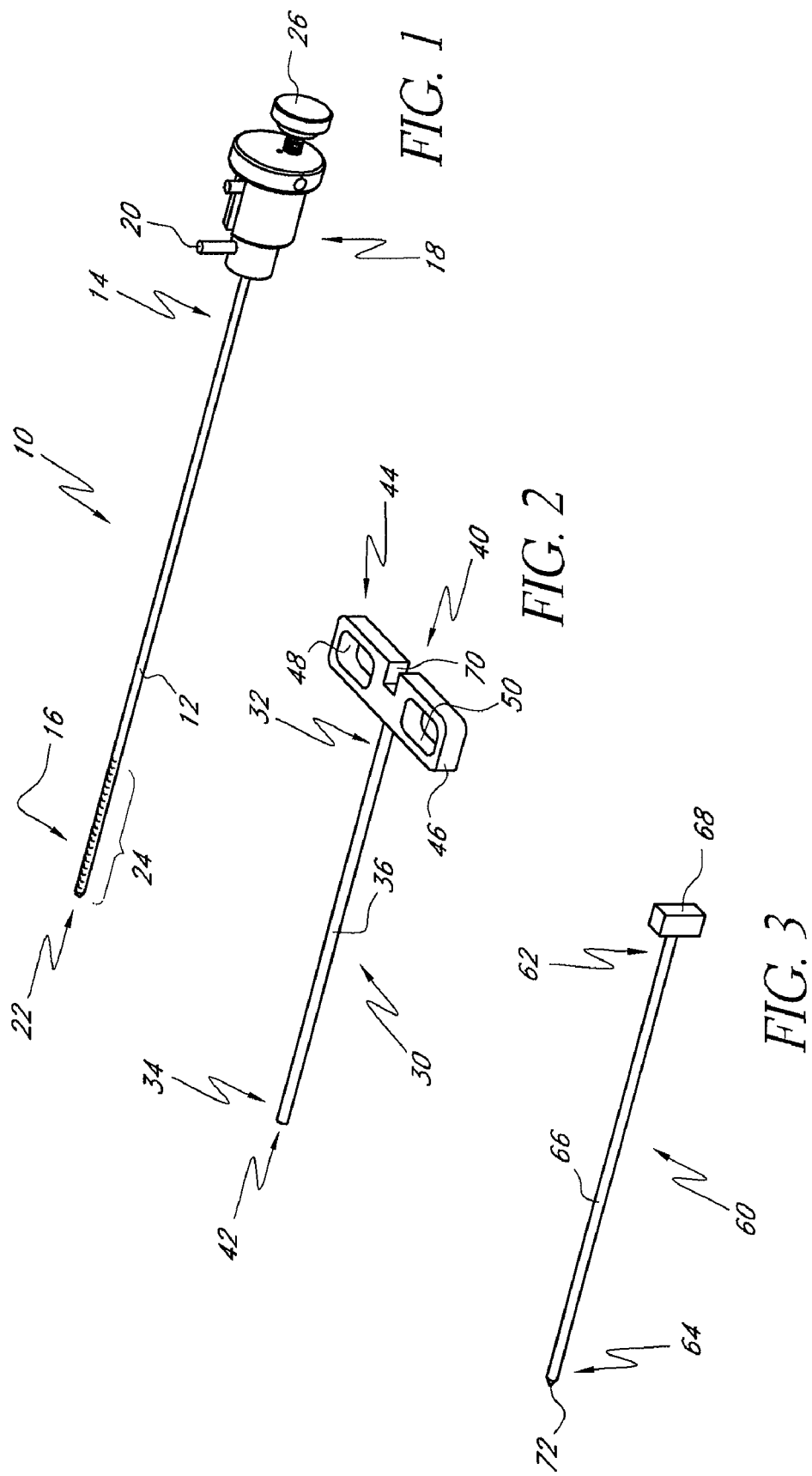

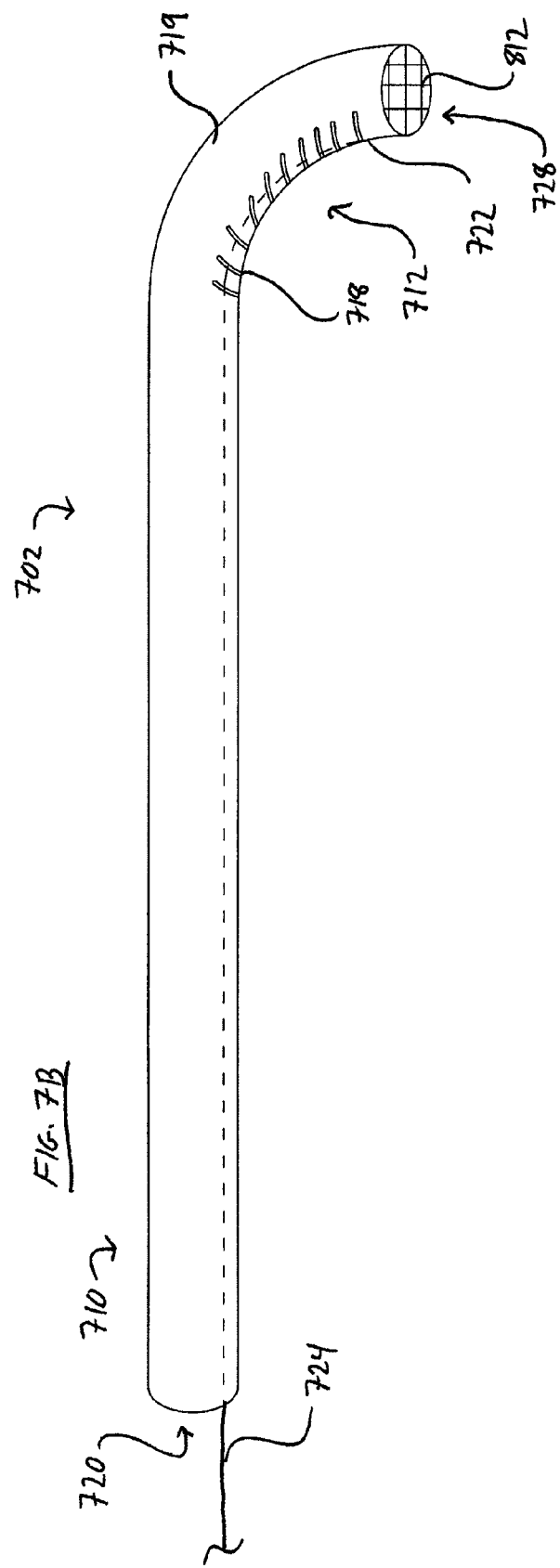

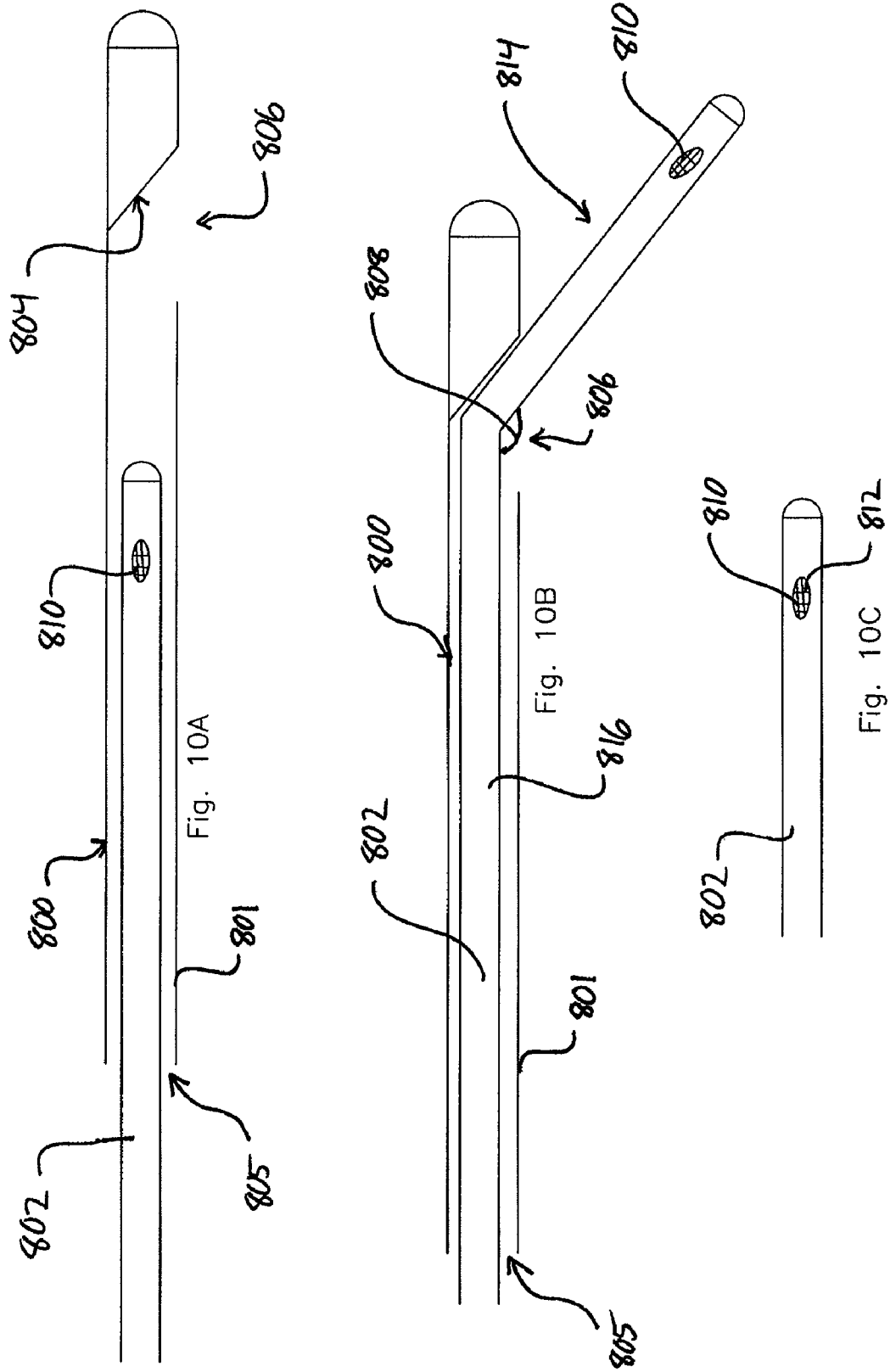

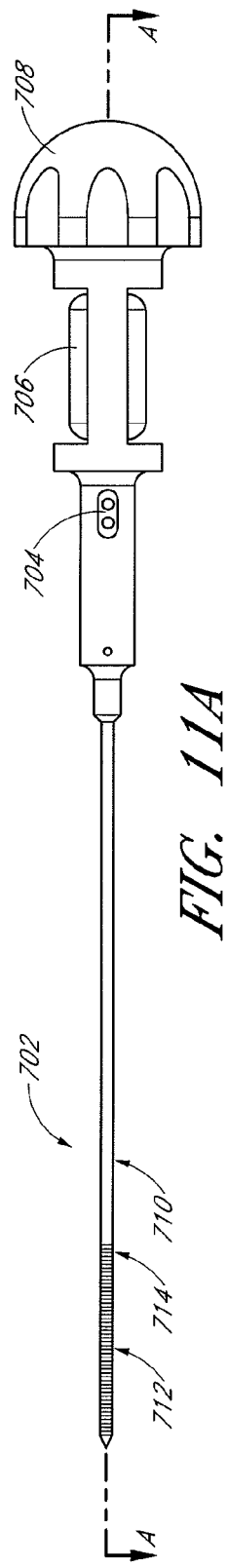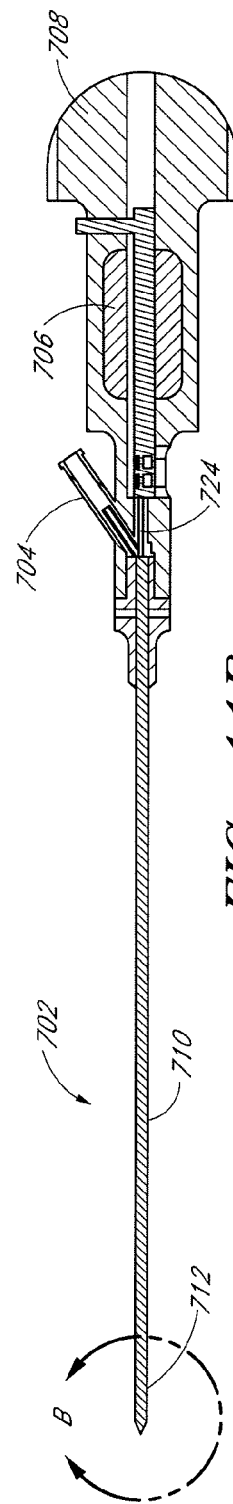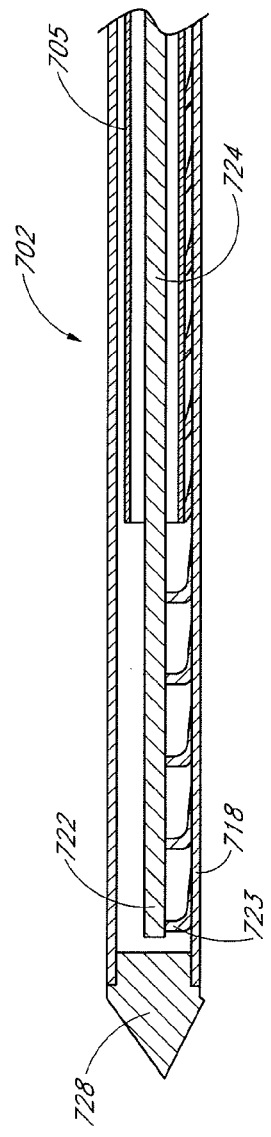

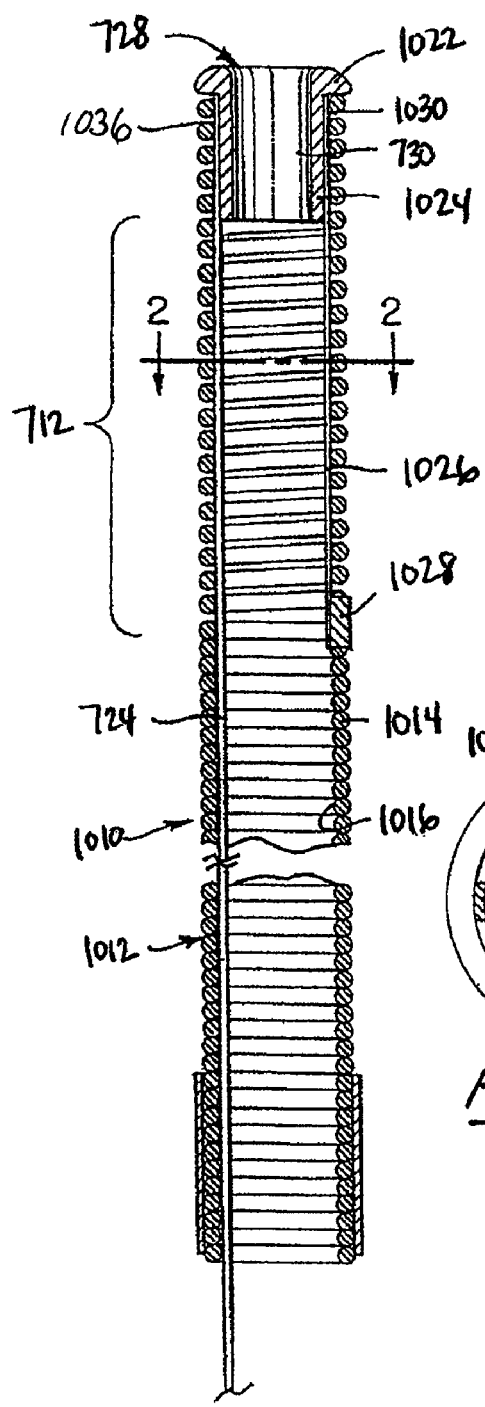
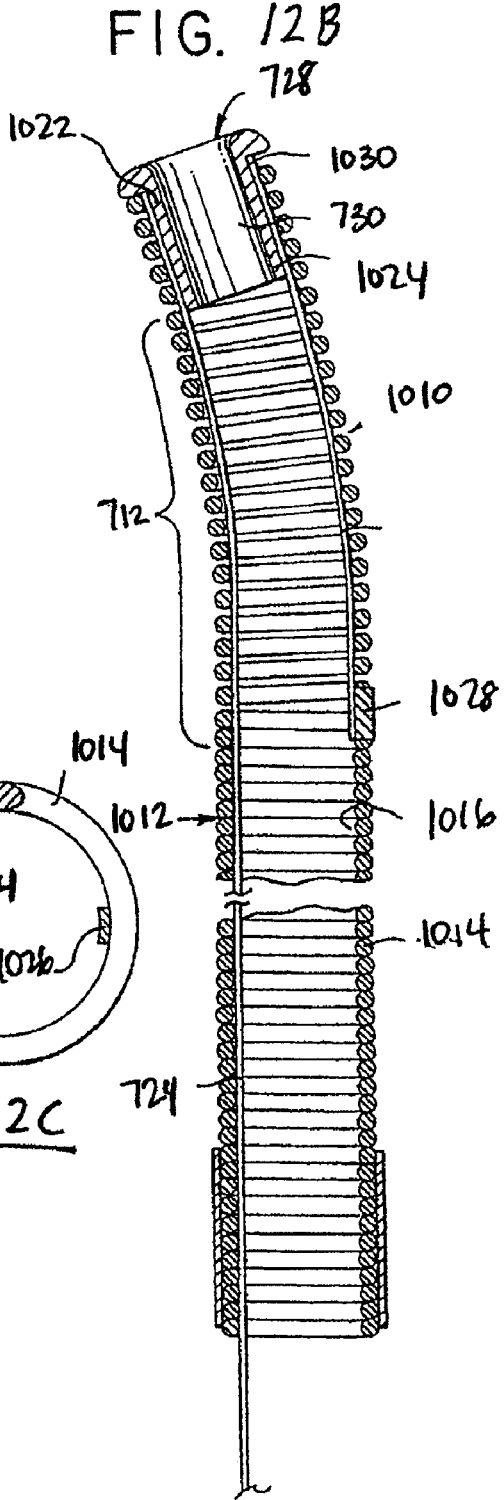

STEERABLE VERTEBROPLASTY SYSTEM

This application claims priority under 35 U.S.C. §120 as a divisional of U.S. patent application Ser. No. 11/941,764, filed on Nov. 16, 2007, currently pending, and incorporated by reference herein in its entirety.

The present invention relates to bone augmentation devices and procedures. In particular, the present invention relates to steerable injection devices and systems for introducing conventional or novel bone cement formulations such as in performing vertebroplasty.

BACKGROUND OF THE INVENTION

According to the National Osteoporosis Foundation ten million Americans have osteoporosis, and an estimated 34 million with low bone mass are at risk of developing osteoporosis (http)://www.nof.org/osteoporosis/diseasefacts.htm). Called the "silent disease," OSP develops slowly over a number of years without symptoms. Eighty percent of those affected are women, particularly petite Caucasian and Asian women, although older men and women of all races and ethnicities are at significant risk.

In the United States, 700,000 people are diagnosed with vertebral compression fractures as a result of OSP each year. Morbidity associated with vertebral fractures includes severe back pain, loss of height and deformity, all of which negatively affect quality of life.

Once microfracture of the vertebra begins, there is little the clinician can do except palliative medical treatment using analgesics, bed rest and/or restriction of activity. With time, the microfractures widen at one level and without surgical intervention, the fractures cascade downward with increasing kyphosis or "hunching" of the back. Once a mechanical lesion develops, surgery is the only option. Vertebroplasty or kyphoplasty are the primary minimally-invasive surgical procedures performed for the treatment of compression-wedge fractures due to OSP.

Vertebroplasty stabilizes the collapsed vertebra by injecting polymethylmethacrylate (PMMA) or a substantially equivalent bone cement into cancellous bone space of the vertebrae. Besides providing structural support to the vertebra, the exothermic reaction of PMMA polymerization is said to kill off the nociceptors or pain receptors in the bone, although no proof of this hypothesis has been provided in the literature. This procedure is typically performed as an outpatient procedure and requires only a short-acting local or general anesthetic. Once the surgical area of the spine is anesthetized, the physician inserts one or two needles through small skin incisions into either the pedicle (uni-transpedicular) or the pedicles of the vertebral body i.e., bi-transpedicular. PMMA is injected through the needle and into the cancellous-bone space of the vertebra.

Kyphoplasty mirrors the vertebroplasty procedure but has the additional step of inserting and expanding a nylon balloon in the interior of the vertebral body. Expansion of the balloon under pressure reduces the compression fracture and creates a cavity. After withdrawal of the balloon, PMMA is injected into the cavity to stabilize the reduction. The kyphoplasty procedure may restore the vertebral body height. Kyphoplasty is an in-patient surgery that requires hospitalization and a general anesthetic. Kyphon Inc. claims over 275,000 spinal fractures have been treated using their PMMA derivative and their "balloon" kyphoplasty procedure worldwide (Sunnyvale, Calif., Sep. 5, 2006, (PR NEWSWIRE) Kyphon study 2006).

Bone cement for both vertebroplasty and kyphoplasty procedures currently employ variations of standard PMMA in a powder and a methyl methacrylate monomer liquid. When the powder and liquid monomer are mixed, an exothermic polymerization takes place resulting in the formation of a "dough-like" material, which is then inserted into the cancellous bone space. The dough, when hardened, becomes either the reinforcing structure or the grout between the bone and prosthesis.

The average clinical in vivo life of the PMMA grout is approximately 10 years due to corrosion fatigue of either the bone-cement/prosthesis and/or the bone cement/bone interfaces. Jasty et al. (1991) showed that in cemented total hip replacements: "Fractures in the cement mantle itself were found on cut sections around all prostheses which had been in use for over three years." Jasty et al. also noted: "In general, specimens less than 10 years in situ showed small incomplete fractures while the specimens in place more than 10 years all showed large complete cement mantle fractures."

When an implant fails, a revision becomes mandatory. After removal of the cement and hardware, a cemented arthroplasty can be repeated if enough cancellous bone matrix exists to grip the new PMMA. Alternatively, cementless prosthesis can be installed. Such a revision, however, can only be applied to total joint replacement failures. For vertebroplasty and/or kyphoplasty, a classical screw and plate internal fixation with autograft fusion is necessary.

Despite advances in the foregoing procedures, there remains a need for improved bone cement delivery systems which enable rapid and controllable deployment of bone cement for the treatment of conditions such as vertebral compression fractures.

SUMMARY OF THE INVENTION

According to one embodiment of the present invention, disclosed is a steerable vertebroplasty device, including an elongate tubular body having a proximal end, a distal end, and a central lumen extending therethrough; a deflectable zone on the distal end of the tubular body, deflectable through an angular range; a handle on the proximal end of the tubular body; and a deflection control on the handle. The handle and deflection control are configured for single hand operation. The deflection control can include a rotatable element. The distal end can include a distally facing exit port in communication with the central lumen, or a laterally facing exit port in some embodiments. The device can also include an actuator extending axially between the deflection control and the deflectable zone. The actuator can be an axially moveable element. The device can also include a port on the proximal end of the vertebroplasty device, in communication with the central lumen. The deflectable zone can be deflectable within a plane, and the port can reside in the same plane. In some embodiments, the tubular body includes a proximal zone and a distal, deflectable zone separated by a transition, and the transition can be at least about 15% of the length of the tubular body from the distal end.

Also disclosed herein is a method of treating a vertebral body. The method includes the steps of introducing a tubular injector having a longitudinal axis through cortical bone and into cancellous bone of a vertebral body; deflecting a distal section of the injector angularly with respect to the longitudinal axis; and introducing media through the injector and into the vertebral body.

In another embodiment, disclosed is a system for performing vertebroplasty. The system includes a steerable injection needle, a cement dispensing pump, and a mixing nozzle. The steerable injection needle has a proximal portion, elongate shaft, and a distal portion, the distal portion movable from a first substantially straight configuration to a second configuration not substantially coaxial with the proximal portion. The cement dispensing pump can include a first cartridge housing configured to house a cartridge containing two separate bone cement components. The mixing nozzle is present for mixing the first bone cement component and second bone cement component material into a bone cement composite. In some embodiments, the system also includes a stylet for creating an access pathway in a pedicle. The system can also include an introducer cannula. The first and/or second bone cement component can also be present in the system. The first bone cement component can include MMA. The second bone cement component can include from about 25% to about 35% by weight of bone particles, or at least about 35% weight percent of bone particles in other embodiments. The steerable injection needle can also include an input port for receiving bone cement from the cement dispensing pump. The input port can include a Luer lock. The steerable injection needle can include an adjustment control configured to adjust the curvature of the distal end. In some embodiments, the steerable injection needle includes an end cap on the distal end of the needle. The steerable injection needle can include a pull wire operably connected to the distal end of the needle. In other embodiments, the steerable injection needle includes a filter operably connected to a distal opening of the needle. The distal portion of the steerable needle can have a working length of at least about 20% of the total working length of the needle. The steerable injection needle may also include a spring coil.

Also disclosed herein is a method of treating a bone, including the steps of creating a pedicular access channel in a pedicle to access the interior of a vertebral body; inserting an introducer cannula into the pedicle; inserting a steerable injection needle through the introducer cannula into the interior of a vertebral body, the steerable injection needle having a proximal end and a distal end, the distal end having a first configuration substantially coaxial with a long axis of the proximal end; deflecting the distal end of the steerable injection needle to a second configuration that is not substantially coaxial with the long axis of the proximal end; and flowing bone cement through the steerable injection needle into the interior of the vertebral body. In some embodiments, the second configuration of the distal end of the steerable injection needle includes a curved portion. In some embodiments, deflecting the distal end of the steerable injection needle is accomplished by exerting tension on a pull wire operably connected to the distal end. In some embodiments, deflecting the distal end of the steerable injection needle is accomplished by withdrawing a sheath at least partially covering the distal end. The method can also include the steps of: providing a cement dispensing pump with a cartridge containing a first bone cement material and a second bone cement material out of contact with the first bone cement material, and a mixing nozzle; flowing the first bone cement material and the second bone cement material into the mixing nozzle, creating a bone cement; and flowing the bone cement into an input port of the steerable injection needle. Flowing bone cement through the steerable injection needle into the interior of the vertebral body can include releasing a first bone cement within the interior of the vertebral body. The bone cement can have at least 35% particles by weight in some embodiments. In some embodiments, flowing bone cement through the steerable injection needle into the interior of the vertebral body additionally includes releasing a second bone cement within the first bone cement, where the second bone cement includes less than about 35% particles by weight.

Also disclosed herein is a closed vertebroplasty bone cement injection system, that includes a cartridge containing at least a first chamber and a second chamber; a first bone cement component in the first chamber and a second bone cement component in the second chamber; a mixing chamber, for mixing the first and second bone cement components; an elongate injection needle, for directing bone cement into a treatment site in the spine; and a closed flow path for directing the first and second bone cement components from the first and second chambers, through the mixing chamber, through the injection needle and into the spine at the treatment site. The cartridge, mixing chamber, and/or injection needle can be releaseably connected to the flow path. The injection needle can have a deflectable distal end.

Also disclosed herein is a method of injecting bone cement into a treatment site in a bone, including the steps of: providing a first chamber having a first bone cement component, and a second chamber having a second bone cement component, the first and second bone cement components formulated to form a hardenable bone cement following mixing; providing a mixing chamber for mixing the first and second bone cement components; providing an elongate, tubular injection needle; connecting the first and second bone cement chambers, the mixing chamber and the injection needle into a closed flow path; and expressing first and second bone cement components through the mixing chamber, through the injection needle and into the site. The first and the second chambers can be contained in a single cartridge.

BRIEF DESCRIPTION OF THE DRAWINGS

FIG. 1 is a perspective view of a steerable injection needle in accordance with one aspect of the present invention.

FIG. 2 is a perspective view of an introducer in accordance with one aspect of the present invention.

FIG. 3 is a perspective view of a stylet in accordance with one aspect of the present invention.

FIG. 7B is a schematic view as in FIG. 7A, following proximal retraction of a pull wire to laterally deflect the distal end.

FIGS. 10A-10C illustrate various aspects of an alternative deflectable needle in accordance with the present invention.

FIGS. 11A-11C illustrate various views of a further embodiment of a deflectable needle in accordance with the present invention.

FIGS. 12A-12C illustrate a distal section of a deflectable needle, comprising a helically wound coil structure.

DETAILED DESCRIPTION OF THE PREFERRED EMBODIMENT

Figure 4:
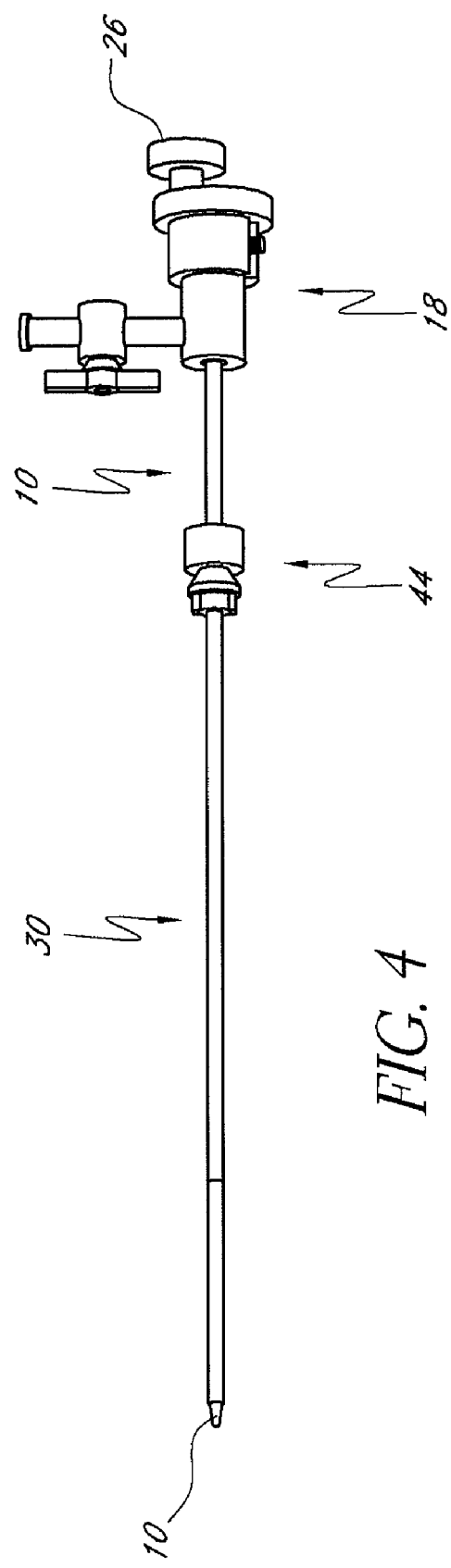
FIG. 4 is a side elevational view of the steerable injection needle moveably coaxially disposed within the introducer, in a substantially linear configuration.

The present invention provides improved delivery systems for delivery of a bone cement or bone cement composite for the treatment of vertebral compression fractures due to osteoporosis (OSP), osteo-trauma, and benign or malignant lesions such as metastatic cancers and myeloma, and associated access and deployment tools and procedures.

The primary materials in the preferred bone cement composite are methyl methacrylate and inorganic cancellous and/or cortical bone chips or particles. Suitable inorganic bone chips or particles are sold by Allosource, Osteotech and LifeNet (K053098); all have been cleared for marketing by FDA The preferred bone cement also may contain the additives: barium sulfate for radio-opacity, benzoyl peroxide as an initiator, N,N-dimethyl-p-toluidine as a promoter and hydroquinone as a stabilizer. Other details of bone cements and systems are disclosed in U.S. patent application Ser. No. 11/626,336, filed Jan. 23, 2007, the disclosure of which is hereby incorporated in its entirety herein by reference.

One preferred bone cement implant procedure involves a two-step injection process with two different concentrations of the bone particle impregnated cement. To facilitate the implant procedure the bone cement materials are packaged in separate cartridges containing specific bone cement and inorganic bone particle concentrations for each step. Tables 1 and 2, infra, list one example of the respective contents and concentrations in Cartridges 1A and 1B for the first injection step, and Cartridges 2A and 2B for the second injection step.

The bone cement delivery system generally includes at least three main components: 1) stylet; 2) introducer cannula; and 3) steerable injection needle. See FIGS. 1-3. Packaged with the system or packaged separately is a cement dispensing pump. The complete system also preferably includes at least one cement cartridge having at least two chambers therein, and a spiral mixing nozzle.

The stylet is used to perforate a hole into the pedicle of the vertebra to gain access to the interior of the vertebral body.

The introducer cannula is used for bone access and as a guide for the steerable injection needle. The introducer cannula is sized to allow physicians to perform vertebroplasty or kyphoplasty on vertebrae with small pedicles such as the thoracic vertebra T5 as well as larger vertebrae. In addition, this system is designed for uni-transpedicular access and/or bi-pedicular access.

Once bone access has been achieved, the steerable injection needle can be inserted through the introducer cannula into the vertebra. The entire interior vertebral body may be accessed using the steerable injection needle. The distal end of the needle can be manually shaped to any desired radius within the product specifications. The radius is adjusted by means of a knob on the proximal end of the device.

The hand-held cement dispensing pump may be attached to the steerable injection needle by a slip-ring luer fitting. The pre-filled 2-chambered cartridges (1A and 1B, and 2A and 2B) are loaded into the dispensing pump. As the handle of the dispensing pump is squeezed, each piston pushes the cartridge material into the spiral mixing tube. The materials are mixed in the spiral mixing nozzle prior to entering the steerable injection needle. The ratio of diameters of the cartridge chambers determines the mixing ratio for achieving the desired viscosity. One particular non-limiting example of an exemplary system is described below.

Delivery System Component Specifications
  Stylet
    Diameter 0.110"±010"
    Length 5.25"±0.125"
    304 stainless steel and/or ABS materials
  Introducer Cannula
    Cannula profile 10 gauge (0.134")
    Cannula length 4.9"±0.125 (124 mm)
    Cannula internal diameter 0.120"±0.002"
    304 stainless steel and/or ABS materials
  Steerable Injection Needle
    Needle profile 12 gauge (0.109") with a 0.077" (1.96 mm) lumen
    Needle working length 7.0"±0.125" (178 mm)
    2.25"±0.125" adjustable section on distal tip
    0.688"±0.125" Minimum needle radius to ∞ (straight)
    Luer fitting for connection to dispensing gun
    304 stainless steel and ABS Hub
  Cement Dispensing Pump and Spiral Mixing Nozzle
    Manual dispensing of cement
    Approximately 10:1 by volume mixing ratio cartridges
    Liquid-Liquid Cartridge 9 mL±0.5 mL
    Real-time mixing through screw nozzle
    Luer fitting for connection to steerable injection needle
    Mixing tube length 2.0"±0.100"
    Mixing tube inside diameter 0.187"±025"
    1000 psi HP (high pressure) Extension Tubing
    Volume per ratchet 0.5 mL+0.25/−0.0 mL The bone cement implant procedures described herein use established vertebroplasty and kyphoplasty surgical procedures to stabilize the collapsed vertebra by injecting bone cement into cancellous bone.

The preferred procedure is designed for uni-transpedicular access and may be accomplished under either a local anesthetic or short-duration general anesthetic. Once the area of the spine is anesthetized, an incision is made and the stylet is used to perforate the vertebral pedicle and gain access to the interior of the vertebral body. The introducer cannula is then inserted and acts as a guide for the steerable injection needle.

Injection of the preferred bone cement involves a two-step procedure. The pre-filled Cartridges 1A and 1B are loaded into the dispensing pump. As the dispensing pump handle is squeezed, each piston pushes material into the spiral mixing tube. The diameter of each chamber may be utilized to determine the mixing ratio for achieving the desired viscosity.

The first step involves injecting a small quantity of PMMA with more than about 35%, e.g., 60% inorganic bone particles, onto the outer periphery of the cancellous bone matrix, i.e., next to the inner wall of the cortical bone of the vertebral body. The cement composite is designed to harden relatively quickly, forming a firm but still pliable shell. This shell is intended to prevent bone marrow/PMMA content from being ejected through any venules or micro-fractures in the vertebral body wall. The second step of the procedure involves a second injection of PMMA with an approximately 30% inorganic bone particles to stabilize the remainder of the weakened, compressed cancellous bone.

Alternatively, the steerable needle disclosed herein and discussed in greater detail below, can be used in conventional vertebroplasty procedures, using a single step bone cement injection.

Injection control for the first and second steps is provided by a 2 mm ID flexible injection needle, which is coupled to the hand operated bone cement injection pump. The 60% (>35%) and 30% ratio of inorganic bone particle to PMMA concentrations may be controlled by the pre-filled cartridge sets 1A and 1B, and 2A and 2B. At all times, the amount of the injectate is under the direct control of the surgeon or intervention radiologist and visualized by fluoroscopy. The introducer cannula is slowly withdrawn from the cancellous space as the second injection of bone cement begins to harden, thus preventing bone marrow/PMMA content from exiting the vertebral body. The procedure concludes with closure of the surgical incision with bone filler. In vitro and in vivo studies have shown that the 60% (>35%) bone-particle impregnated bone cement hardens in 2-3 minutes and 30% bone-particle impregnated bone cement hardens between 4 to 10 minutes.

Details of the system components will be discussed below.

There is provided in accordance with the present invention a steerable injection device that can be used to introduce any of a variety of materials or devices for diagnostic or therapeutic purposes. In one embodiment, the system is used to inject bone cement, e.g., PMMA or any of the bone cement compositions disclosed elsewhere herein. The injection system most preferably includes a tubular body with a steerable (i.e., deflectable) distal portion for introducing bone cement into various locations displaced laterally from the longitudinal axis of the device within a vertebral body during a vertebroplasty procedure.

Referring to FIG. 1, there is illustrated a side perspective view of a steerable injection needle 10 in accordance with one aspect of the present invention. The steerable injection needle 10 comprises an elongate tubular body 12 having a proximal end 14 and a distal end 16. The proximal end 14 is provided with a handle or manifold 18, adapted to remain outside of the patient and enable introduction and/or aspiration of bone cement or other media, and control of the distal end as will be described herein. In general, manifold 18 is provided with at least one injection port 20, which is in fluid communication with a central lumen (not illustrated) extending through tubular body 12 to at least one distal exit port 22.

The manifold 18 is additionally provided with a control 26 such as a rotatable knob, slider, or other moveable control, for controllably deflecting a deflection zone 24 on the distal end 16 of the tubular body 12. As is described elsewhere herein, the deflection zone 24 may be advanced from a relatively linear configuration as illustrated in FIG. 1 to a deflected configuration throughout an angular range of motion.

Referring to FIG. 2, there is illustrated an elongate tubular introducer 30, having a proximal end 32, a distal end 34 and an elongate tubular body 36 extending therebetween. A central lumen 38 (not shown) extends between a proximal access port 40 and a distal access port 42.

The central lumen 38 has an inside diameter which is adapted to slideably axially receive the steerable injection needle 10 therethrough. This enables placement of the distal end 34 adjacent a treatment site within the body, to establish an access pathway from outside of the body to the treatment site. As will be appreciated by those of skill in the art, the introducer 30 enables procedures deep within the body such as within the spine, through a minimally invasive and/or percutaneous access. The steerable injection needle 10 and/or other procedure tools may be introduced into port 40, through lumen 38 and out of port 42 to reach the treatment site.

The proximal end 32 of introducer 30 may be provided with a handle 44 for manipulation during the procedure. Handle 44 may be configured in any of a variety of ways, such as having a frame 46 with at least a first aperture 48 and a second aperture 50 to facilitate grasping by the clinician.

Referring to FIG. 3, there is illustrated a perspective view of stylet 60. Stylet 60 comprises a proximal end 62, a distal end 64 and an elongate body 66 extending therebetween. The proximal end 62 may be provided with a stop 68 such as a grasping block, manifold or other structure, to facilitate manipulation by the clinician. In the illustrated embodiment, the block 68 is configured to nest within a recess 70 on the proximal end of the introducer 30.

As will be appreciated by those of skill in the art, the stylet 60 has an outside diameter which is adapted to coaxially slide within the central lumen on introducer 30. When block 68 is nested within recess 70, a distal end 64 of stylet 60 is exposed beyond the distal end 34 of introducer 30. The distal end 64 of stylet 60 may be provided with a pointed tip 72, such as for anchoring into the surface of a bone.

Referring to FIG. 4, there is illustrated a side elevational view of an assembly in accordance with the present invention in which a steerable injection needle 10 is coaxially positioned within an introducer 30. The introducer 30 is axially moveably carried on the steerable injection needle 10. In the illustration of FIG. 4, the introducer 30 is illustrated in a distal position such that it covers at least a portion of the deflection zone 24 on injection needle 10.

Figure 5:
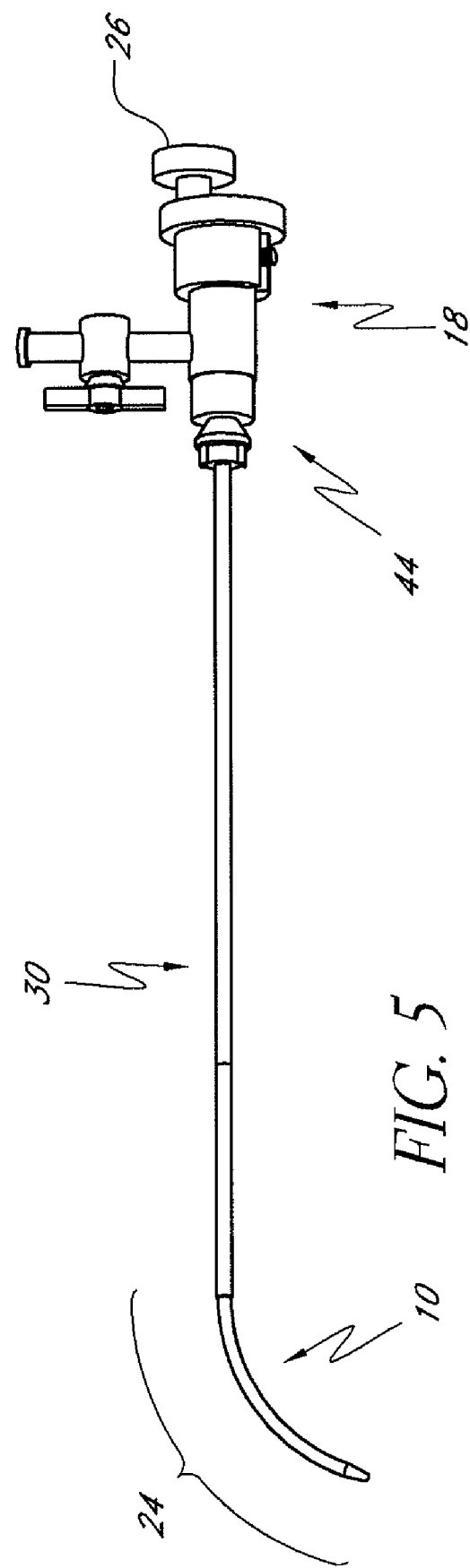
FIG. 5 is a side elevational view of the assembly of FIG. 4, showing the steerable injection needle in a curved configuration.

FIG. 5 illustrates an assembly as in FIG. 4, in which the introducer 30 has been proximally retracted along the injection needle 10 to fully expose the deflection zone 24 on injection needle 10. In addition, the control 26 has been manipulated to deflect the deflection zone 24 through an angle of approximately 90°. Additional details of the steerable needle will be discussed below.

Figure 6:
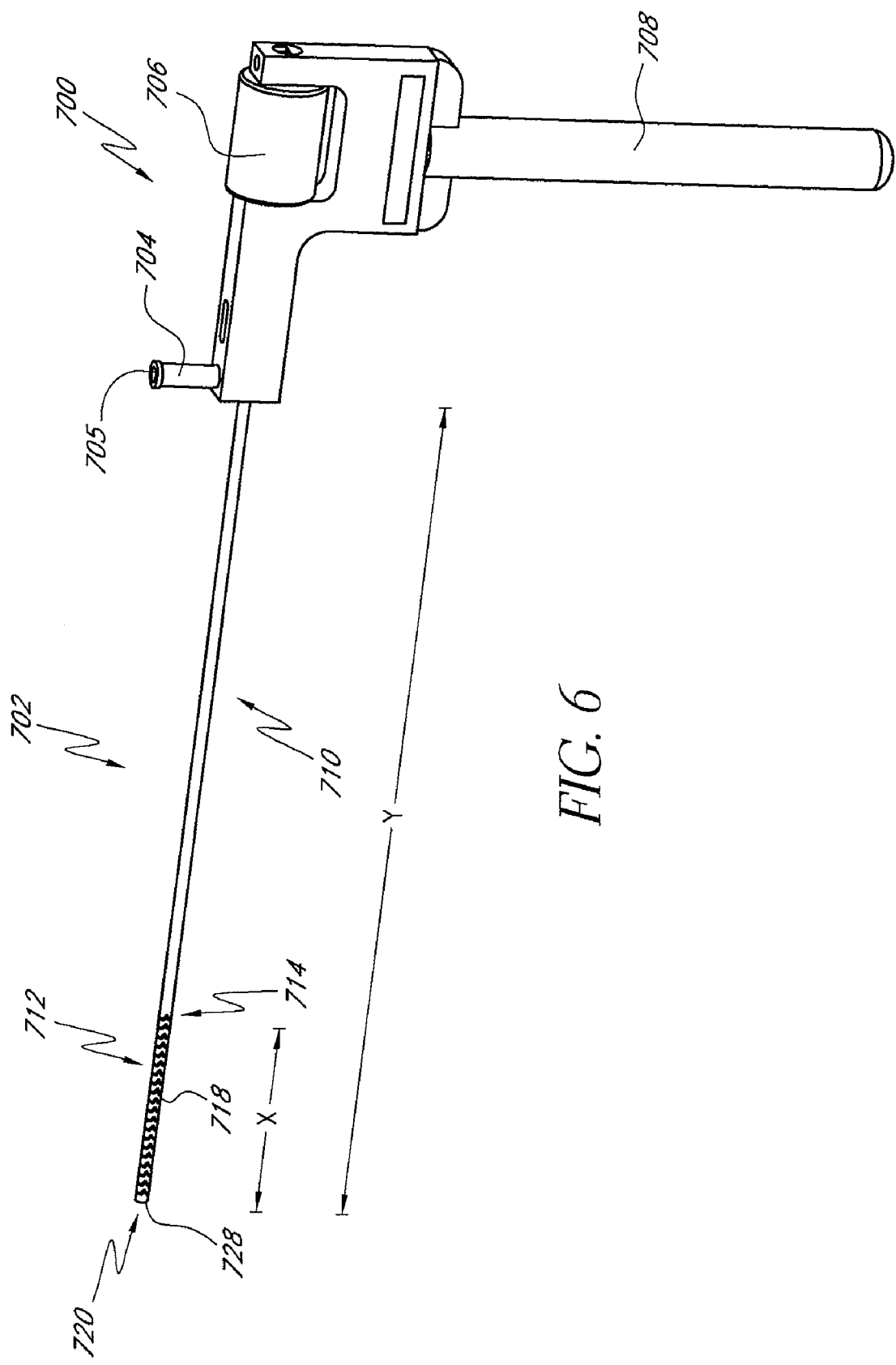
FIG. 6 is a side elevational schematic view of another steerable injection needle in accordance with the present invention.

FIG. 6 illustrates a schematic perspective view of an alternate steerable vertebroplasty injector, according to one embodiment of the invention. The steerable injector 700 includes a body or shaft portion 702 that is preferably elongate and tubular, input port 704, adjustment control 706, and handle portion 708. The elongate shaft 702 preferably has a first proximal portion 710 and a second distal portion 712 which merge at a transition point 714. Shaft 702 may be made of stainless steel, such as 304 stainless steel, Nitinol, Elgiloy, or other appropriate material. Alternatively, the tubular body 702 may be extruded from any of a variety of polymers well known in the catheter arts, such as PEEK, PEBAX, nylon and various polyethylenes. Extruded tubular bodies 702 may be reinforced using metal or polymeric spiral wrapping or braided wall patterns, as is known in the art.

The shaft 702 defines at least one lumen therethrough that is preferably configured to carry a flowable bone cement prior to hardening. Proximal portion 710 of shaft 702 is preferably relatively rigid, having sufficient column strength to push through cancellous bone. Distal portion 712 of shaft 702 is preferably flexible and/or deflectable and reversibly actuatable between a relatively straight configuration and one or more deflected configurations or curved configurations as illustrated, for example, in FIG. 5, as will be described in greater detail below. The distal portion 712 of shaft 702 may include a plurality of transverse slots 718 that extend partially circumferentially around the distal portion 712 of the shaft 702 to provide a plurality of flexion joints to facilitate bending.

Input port 704 may be provided with a Luer lock connector although a wide variety of other connector configurations, e.g., hose barb or slip fit connectors can also be used. Lumen 705 of input port 704 is fluidly connected to central lumen 720 of shaft 702 such that material can flow from a source, through input port 704 into central lumen 720 of the shaft 702 and out the open distal end or out of a side opening on distal portion 712. Input port 704 is preferably at least about 20 gauge and may be at least about 18, 16, 14, or 12 gauge or larger in diameter.

Input port 704 advantageously allows for releasable connection of the steerable injection device 700 to a source of hardenable media, such as a bone cement mixing device described herein. In some embodiments, a plurality of input ports 704, such as 2, 3, 4, or more ports are present, for example, for irrigation, aspiration, introduction of medication, hardenable media precursors, hardenable media components, catalysts or as a port for other tools, such as a light source, cautery, cutting tool, visualization devices, or the like. A first and second input port may be provided, for simultaneous introduction of first and second bone cement components such as from a dual chamber syringe or other dispenser. A mixing chamber may be provided within the injection device 700, such as within the proximal handle, or within the tubular shaft 702

A variety of adjustment controls 706 may be used with the steerable injection system, for actuating the curvature of the distal portion 712 of the shaft 702. Preferably, the adjustment control 706 advantageously allows for one-handed operation by a physician. In one embodiment, the adjustment control 706 is a rotatable member, such as a thumb wheel or dial. The dial can be operably connected to a proximal end of an axially movable actuator such as pull wire 724. See FIG. 7A. When the dial is rotated in a first direction, a proximally directed tension force is exerted on the pull wire 724, actively changing the curvature of the distal portion 712 of the shaft 702 as desired. The degree of deflection can be observed fluoroscopically, and/or by printed or other indicium associated with the control 706. Alternative controls include rotatable knobs, slider switches, compression grips, triggers such as on a gun grip handle, or other depending upon the desired functionality.

In some embodiments, the adjustment control 706 allows for continuous adjustment of the curvature of the distal portion 712 of shaft 702 throughout a working range. In other embodiments, the adjustment control is configured for discontinuous (i.e., stepwise) adjustment, e.g., via a ratcheting mechanism, preset slots, deflecting stops, a rack and pinion system with stops, ratcheting band (adjustable zip-tie), adjustable cam, or a rotating dial of spring loaded stops. In still other embodiments, the adjustment control 706 may include an automated mechanism, such as a motor or hydraulic system to facilitate adjustment.

The adjustment control may be configured to allow deflection of the distal portion 712 through a range of angular deviations from 0 degrees (i.e., linear) to at least about 15°, and often at least about 25°, 35°, 60°, 90°, 120°, 150°, or more degrees from linear.

In some embodiments, the length X of the flexible distal portion 712 of shaft 702 is at least about 10%, in some embodiments at least about 15%, 25%, 35%, 45%, or more of the length Y of the entire shaft 702 for optimal delivery of bone cement into a vertebral body. One of ordinary skill in the art will recognize that the ratio of lengths X:Y can vary depending on desired clinical application. In some embodiments, the maximum working length of needle 702 is no more than about 15", 10", 8", 7", 6", or less depending upon the target and access pathway. In one embodiment, when the working length of needle 702 is no more than about 8", the adjustable distal portion 712 of shaft has a length of at least about 1" and preferably at least about 1.5" or 2".

Figure 7A:
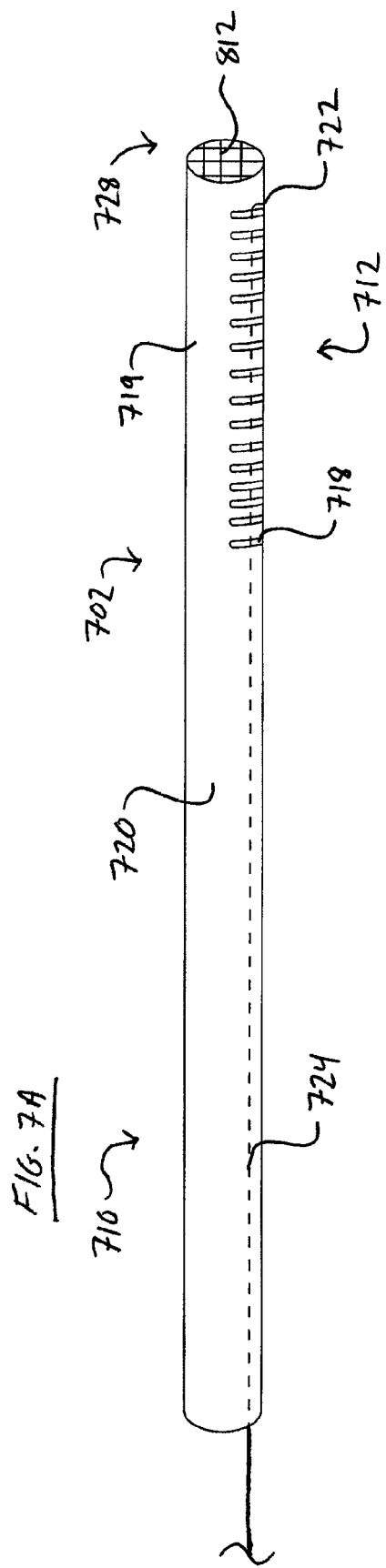
FIG. 7A is a schematic view of a distal portion of the steerable needle of FIG. 6, shown in a linear configuration.

FIGS. 7A-B are schematic perspective views of a distal portion of shaft 702 of a steerable vertebroplasty injector, according to one embodiment of the invention. Shown is the preferably rigid proximal portion 710 and deflectable distal portion 712. The distal portion 712 of shaft 702 includes a plurality of transverse slots 718 that extend partially circumferentially around the distal portion 712 of the shaft 702, leaving a relatively axially non-compressible spine 719 in the form of the unslotted portion of the tubular wall.

In some embodiments, the slots 718 can be machined or laser cut out of the tube stock that becomes shaft 702, and each slot may have a linear, chevron or other shape. In other embodiments, the distal portion 712 of shaft 702 may be created from an elongate coil rather than a continuous tube.

Slots 718 provide small compression hinge joints to assist in the reversible deflection of distal portion 712 of shaft 702 between a relatively straightened configuration and one or more curved configurations. One of ordinary skill in the art will appreciate that adjusting the size, shape, and/or spacing of the slots 718 can impart various constraints on the radius of curvature and/or limits of deflection for a selected portion of the distal portion 712 of shaft 702. For example, the distal portion 712 of shaft 702 may be configured to assume a second, fully deflected shape with a relatively constant radius of curvature throughout its length. In other embodiments, the distal portion 712 may assume a progressive curve shape with a variable radius of curvature which may, for example, have a decreasing radius distally. In some embodiments, the distal portion may be laterally displaced through an arc having a radius of at least about 0.5", 0.75", 1.0", 1.25", or 1.5" minimum radius (fully deflected) to ∞ (straight) to optimize delivery of bone cement within a vertebral body. Wall patterns and deflection systems for bendable slotted tubes are disclosed, for example, in U.S. Pat. Nos. 5,378,234 or 5,480,382 to Hammerslag et al., the disclosures of which are incorporated in its entirety by reference herein.

Still referring to FIGS. 7A-B, a pull wire 724 resides within the lumen 720 of shaft 702. The distal end 722 of the pull wire 724 is preferably operably attached, such as by adhesive, welding, soldering, crimping or the like, to an inner side wall of the distal portion 712 of the shaft 702. Preferably, the attachment point will be approximately 180° offset from the center of the axially extending spine 719. Proximal portion of pull wire 724 is preferably operably attached to adjustment control 706. The adjustment control 706 may be configured to provide an axial pulling force in the proximal direction toward the proximal end of pull wire 724. This in turn exerts a proximal traction on the distal portion 712 of shaft 702 operably attached to distal end 722 of pull wire 724. The slotted side of the tubular body shortens under compression, while the spine side 719 retains its axial length causing the distal portion 712 of shaft 702 to assume a relatively curved or deflected configuration. In some embodiments, a plurality of pull wires, such as two, three, four, or more pull wires 724 may be present within the lumen 720 with distal points of attachment spaced axially apart to allow the distal portion 712 of shaft 702 to move through compound bending curves depending on the desired bending characteristic. Distal axial advance of the actuator will cause a deflection in an opposite direction, by increasing the width of the slots 718.

Figure 8:
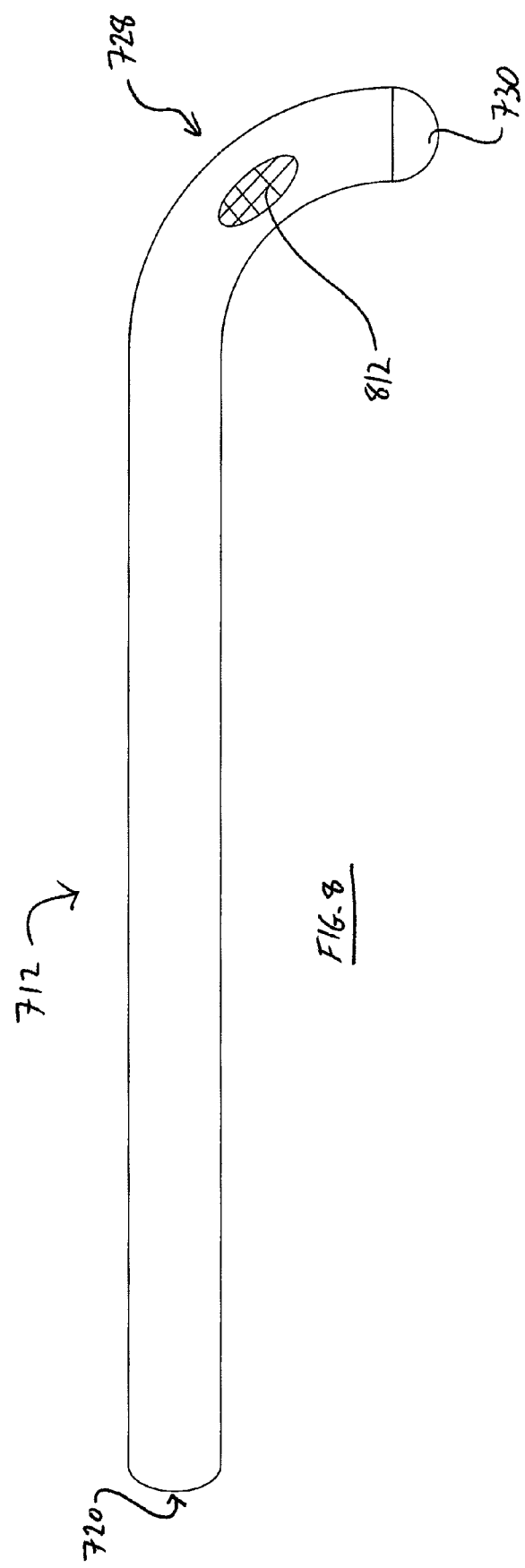
FIG. 8 is a schematic view of a distal portion of a steerable needle, having a side port.

A distal opening 728 is provided on shaft 702 in communication with central lumen 720 to permit expression of material, such as bone cement, from the injector 700. Some embodiments may include a filter such as mesh 812. Mesh structure 812 can advantageously control cement output by controlling bubbles and/or preventing undesired large or unwieldy aggregations of bone cement from being released at one location and thus promote a more even distribution of bone cement within the vertebral body. The mesh 812 may be created by a laser-cut crisscrossing pattern within distal end as shown, or can alternatively be separately formed and adhered, welded, or soldered on to the distal opening 728. Referring to FIG. 8, the distal shaft portion 712 may also include an end cap 730 or other structure for occluding central lumen 720, and a distal opening 728 on the sidewall of shaft 702.

In some embodiments, the distal shaft 712 can generate a lateral force of at least about 0.125 pounds, 0.25 pounds, 0.5 pounds, 1 pound, 1.5 pounds, 2 pounds, 3 pounds, 4 pounds, 5 pounds, 6 pounds, 7 pounds, 8 pounds, 9 pounds, 10 pounds, or more by activating control 706. This can be advantageous to ensure that the distal portion 712 is sufficiently navigable laterally through cancellous bone to distribute cement to the desired locations. In some embodiments, the distal shaft 712 can generate a lateral force of at least about 0.125 pounds but no more than about 10 pounds; at least about 0.25 pounds but no more than about 7 pounds; or at least about 0.5 pounds but no more than about 5 pounds.

In some embodiments, the distal portion 712 of shaft 702 (or end cap 730) has visible indicia, such as, for example, a marker visible via one or more imaging techniques such as fluoroscopy, ultrasound, CT, or MRI.

Figure 9A:
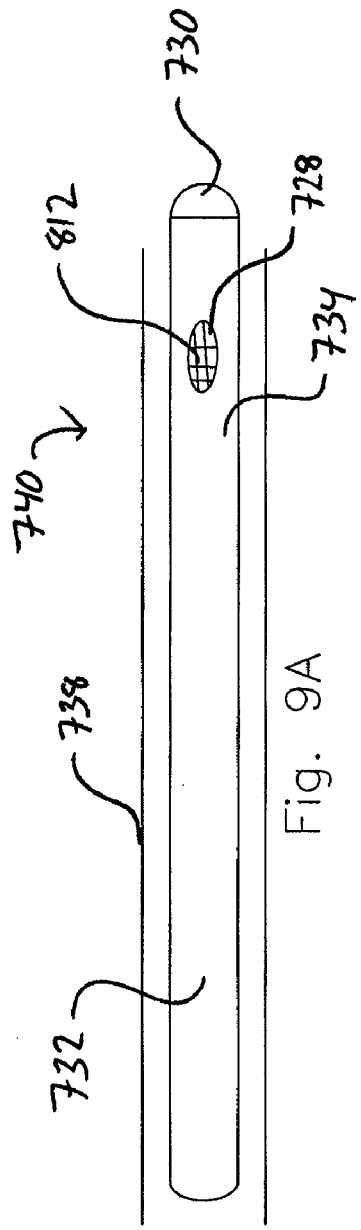
FIG. 9A is a schematic view of a distal portion of a steerable needle, positioned within an outer sheath.
Figure 9B:
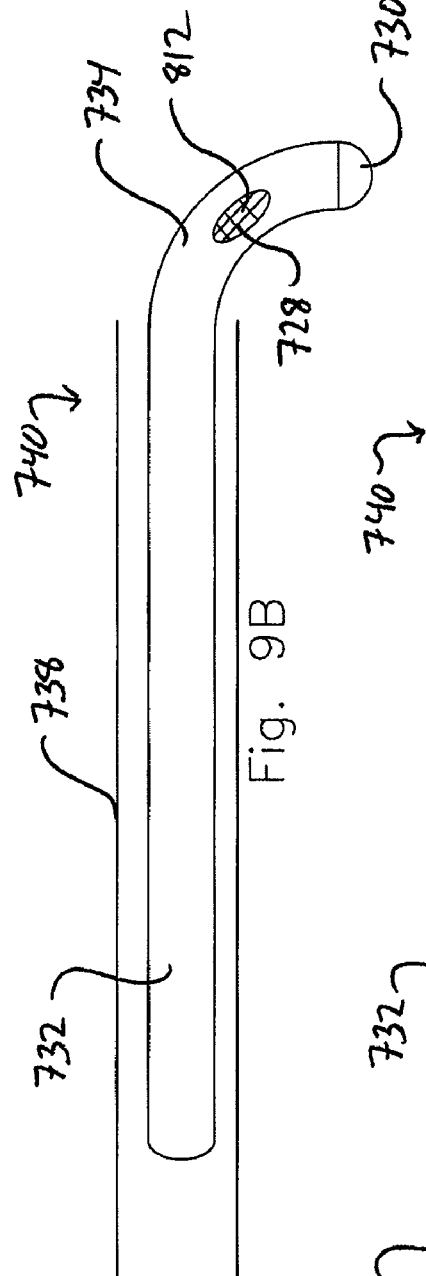
FIG. 9B is an illustration as in FIG. 9A, with the distal sheath partially proximally retracted.
Figure 9C:
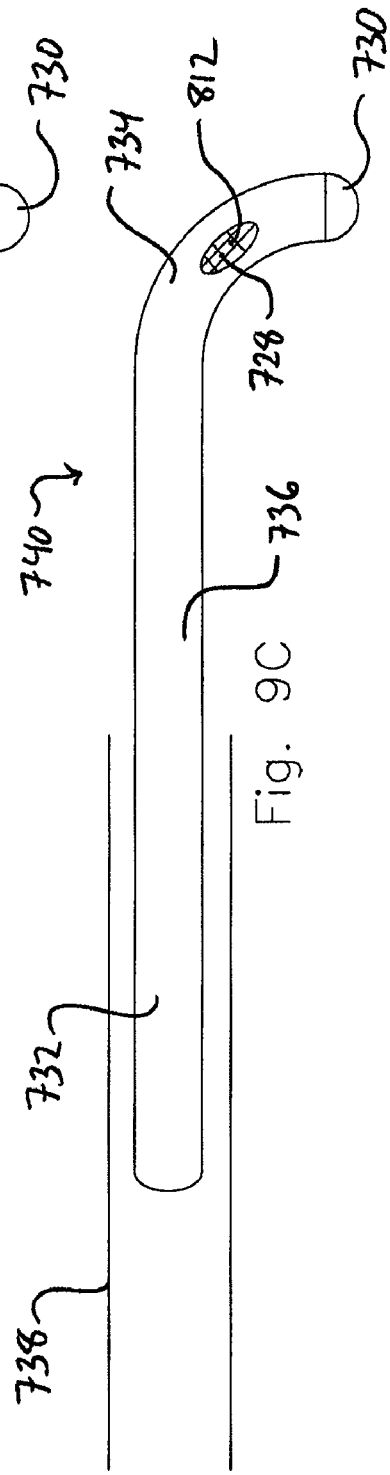
FIG. 9C is an illustration as in FIG. 9B, with the outer sheath proximally retracted a sufficient distance to fully expose the deflection zone.

FIGS. 9A-C illustrate in schematic cross-section another embodiment of a distal portion 734 of a steerable injection device 740. The tubular shaft 736 can include a distal portion 734 made of or containing, for example, a shape memory material that is biased into an arc when in an unconstrained configuration. Some materials that can be used for the distal curved portion 734 include Nitinol, Elgiloy, stainless steel, or a shape memory polymer. A proximal portion 732 of the shaft 736 is preferably relatively straight as shown. Also shown is end cap 730, distal lateral opening 728 and mesh 812.

The distal curved portion 734 may be configured to be axially movably received within an outer tubular sheath 738. The sheath 738 is preferably configured to have sufficient rigidity and radial strength to maintain the curved distal portion 734 of shaft 732 in a relatively straightened configuration while the outer tubular sheath 738 coaxially covers the curved distal portion 734. Sheath 738 can be made of, for example, a metal such as stainless steel or various polymers known in the catheter arts. Axial proximal withdrawal of the sheath 738 with respect to tubular shaft 736 will expose an unconstrained portion of the shape memory distal end 734 which will revert to its unstressed arcuate configuration. Retraction of the sheath 738 may be accomplished by manual retraction by an operator at the proximal end, retraction of a pull wire attached to a distal portion of the sheath 738, or other ways as known in the art. The straightening function of the outer sheath 738 may alternatively be accomplished using an internal stiffening wire, which is axially movably positionable within a lumen extending through the tubular shaft 736. The length, specific curvature, and other details of the distal end may be as described elsewhere herein.

In another embodiment, as shown in FIGS. 10A-C, tubular shaft 802 of a steerable vertebroplasty injector may be generally substantially straight throughout its length in its unstressed state, or have a laterally biased distal end. A distally facing or side facing opening 810 is provided for the release of a material, such as bone cement. In this embodiment, introducer 800 includes an elongate tubular body 801 with a lumen 805 therethrough configured to receive the tubular shaft (also referred to as a needle) 802. Introducer 800 can be made of any appropriate material, such as, stainless steel and others disclosed elsewhere herein. Needle 802 may be made of a shape memory material, such as nitinol, with superelastic properties, and has an outside diameter within the range of between about 1 to about 3 mm, about 1.5-2.5 mm, or about 2.1 mm in some embodiments.

Introducer 800 includes a needle-redirecting element 804 such as an inclined surface near its distal end. Needle-redirecting element 804 can be, for example, a laser-cut tang or a plug having a proximal surface configured such that when needle 802 is advanced distally into introducer 800 and comes in contact with the needle-redirecting element 804, a distal portion 814 of needle 802 is redirected out an exit port 806 of introducer 800 at an angle 808, while proximal portion 816 of needle 802 remains in a relatively straightened configuration, as shown in FIG. 10B. Bone cement can then be ejected from distal opening 810 on the end or side of needle 802 within bone 1000. Distal opening 810 may be present at the distal tip of the needle 802 (coaxial with the long axis of the needle 802) or alternatively located on a distal radial wall of needle 802 as shown in FIG. 10C. In some embodiments, the angle 808 is at least about 15 degrees and may be at least about 30, 45, 60, 90, 105 degrees or more with respect to the long axis of the introducer 800.

The illustrated embodiment of FIGS. 10A-C and other embodiments disclosed herein are steerable through multiple degrees of freedom to distribute bone cement to any area within a vertebral body. For example, the introducer 800 and needle 802 can both rotate about their longitudinal axes with respect to each other, and needle 802 can move coaxially with respect to the introducer 800, allowing an operator to actuate the injection system three dimensionally. The distal portion 814 of needle 802 can be deflected to a position that is angularly displaced from the long axis of proximal portion 816 of needle without requiring a discrete curved distal needle portion as shown in other embodiments herein.

FIGS. 11A-C illustrate another embodiment of a steerable vertebroplasty injector. FIG. 11A schematically shows handle portion 708, adjustment control 706, and elongate needle shaft 702, including proximal portion 710, distal portion 712, and transition point 714. FIG. 11B is a vertical cross-section through line A-A of FIG. 11A, and shows adjustment control 706 operably connected to pull wire 724 such as through a threaded engagement. Also shown is input port 704, and proximal portion 710 and distal portion 712 of needle shaft 702. FIG. 11C illustrates a cross-sectional view of distal portion 712 of shaft 702. The distal end 722 of pull wire 724 is attached at an attachment point 723 to the distal portion 712 of shaft 702. Proximal retraction on pullwire 724 will collapse transverse slots 718 and deflect the injector as has been discussed. Also shown is an inner tubular sleeve 705, which can be advantageous to facilitate negotiation of objects or media such as bone cement, through the central lumen of the needle shaft 702.

The interior sleeve 705 is preferably in the form of a continuous, tubular flexible material, such as nylon or polyethylene. In an embodiment in which the needle 702 has an outside diameter of 0.095 inches (0.093 inch coil with a 0.001 inch thick outer sleeve) and an inside diameter of 0.077 inches, the interior tubular sleeve 705 may have an exterior diameter in the area of about 0.074 inches and an interior diameter in the area of about 0.069 inches. The use of this thin walled tube 705 on the inside of the needle shaft 702 is particularly useful for guiding a fiber through the needle shaft 702. The interior tube 705 described above is additionally preferably fluid-tight, and can be used to either protect the implements transmitted therethrough from moisture, or can be used to transmit bone cement through the steerable needle.

In some embodiments, an outer tubular coating or sleeve (not shown) is provided for surrounding the steerable needle shaft at least partially throughout the distal end of the needle. The outer tubular sleeve may be provided in accordance with techniques known in the art and, in one embodiment, is a thin wall polyester (e.g., ABS) heat shrink tubing such as that available from Advanced Polymers, Inc. in Salem, N.H. Such heat shrink tubings have a wall thickness of as little as about 0.0002 inches and tube diameter as little as about 0.010 inches. The outer tubular sleeve enhances the structural integrity of the needle, and also provides a fluid seal and improved lubricity at the distal end over embodiments with distal joints 718. Furthermore, the outer tubular sleeve tends to prevent the device from collapsing under a proximal force on a pull wire. The sleeve also improves pushability of the tubular members, and improves torque transmission.

In other embodiments, instead of a slotted tube, the needle shaft of a vertebroplasty injection system may include a metal or polymeric coil. Steerable helical coil-type devices are described, for example, in U.S. Pat. Nos. 5,378,234 or 5,480,382 to Hammerslag et al., which are both incorporated by reference herein in their entirety. As shown in FIGS. 12A-C, steerable sheath 1010 includes an elongate tubular body 1012 which is laterally flexible at least in the distal steering region thereof. Tubular body 1012 generally includes a spring coil portion 1014 as known in the art. Spring coil 1014 may additionally be coupled to a proximal hypodermic needle tubing section. Spring coil 1014 defines a central elongate lumen 1016 for guiding materials, such as bone cement axially through the sheath and out a distal opening 728. In some embodiments, an end cap 730 may be provided. End cap 730 may be preferably additionally provided with one or more axially extending support structures such as annular flange 1024 which extends in a proximal direction through central lumen 1016 to securely anchor end cap 730. Axial flange 1024 and radial flange 1022 can be mounting surfaces for attachment of a deflection wire 1026 and pull ribbon 724 as will be discussed.

Portion of spring coil 1014 which extends around axial flange 1024 is relatively inflexible. Thus, the axial length of flange 1024 can be varied to affect the deflected profile of the steerable sheath 1010. A deflection wire 1026 or other column support enhancing element is preferably secured with respect to a relatively noncompressible portion of tubular body 1012 at a proximal point 1028 and extends distally to a distal point of attachment 1030 to provide column strength. The distal point of attachment may secure the deflection wire 1026 to either or both of the spring coil 1014 and end cap 730. Deflection wire 1026 bends upon axial displacement of pull wire 724, with proximal point of attachment 1028 functioning as a fulcrum or platform.

Proximal attachment 1028 may be a solder, braze or weld joint, as is known in the art, with any excess on the radial outside surface of the tubular body 1012 being trimmed or polished to minimize rough edges. Distal point of attachment 1030 is similarly provided by any of a variety of conventional securing techniques which is appropriate for the construction materials of the steerable sheath 1010.

The length of the space between the proximal point of attachment 1028 and distal point of attachment 1030 affects the radius of the curve of the deflection wire 1026 and hence of the region 712, as will be appreciated by one of skill in the art. The deflection wire 1026 will tend to remain positioned along the exterior circumference of the curve during deflection by axial compression of the steerable sheath 1010. Since the circumference in a given steerable sheath 1010 will be a fixed distance, the radius of the curve during deflection will differ, depending upon the degree of deflection achieved.

Deflection at distal steering region 712 of steerable sheath 1010 is accomplished by providing a pull wire 724. Pull wire 724 is preferably secured at a distal point of attachment 1036 and extends proximally to the control end of the steerable sheath 1010. Axial displacement of the pull wire 724 will tend to pivot the steering region 712 of the tubular body 1012 around proximal point of attachment 1028, as shown in FIG. 12B. Preferably, lateral displacement of steering region 712 is accomplished by axial proximal displacement of pull wire 724.

Pull wire 724 is rotationally offset from deflection wire 1026 by at least about 90°. Preferably, pull wire 724 is rotationally offset from deflection wire 1026 by about 180°, as illustrated in FIGS. 12A-B and cross-sectional view FIG. 12C. Among other advantages of this configuration, opposing placement of deflection wire 1026 and pull wire 1035 tends to maintain central lumen 1016 open while the steering region 712 is laterally deflected in response to proximal displacement of pull wire 724. This tends to optimize the flowability of bone cement through the central lumen.

In another embodiment, an interior tubular sleeve (not illustrated) is additionally provided to facilitate flow of media through central lumen 1016 as described elsewhere in the application. In some embodiments, a heat-shrink outer tubular sleeve as described elsewhere in the application is also provided to enhance the structural integrity of the sheath, provide a fluid seal, as well as improve lubricity.

In one embodiment, the steerable injection needle (also referred to as the injection shaft) has an outside diameter of between about 8 to 24 gauge, more preferably between about 10 to 18 gauge, e.g., 12 gauge, 13 gauge (0.095" or 2.41 mm), 14 gauge, 15 gauge, or 16 gauge. In some embodiments, the inside diameter (luminal diameter) of the injection needle is between about 9 to 26 gauge, more preferably between about 11 to 19 gauge, e.g., 13 gauge, 14 gauge, 15 gauge, 16 gauge, or 17 gauge. In some embodiments, the inside diameter of the injection needle is no more than about 4 gauge, 3 gauge, 2 gauge, or 1 gauge smaller than the outside diameter of the injection needle.

The inside luminal diameter of all of the embodiments disclosed herein is preferably optimized to allow a minimal exterior delivery profile while maximizing the amount of bone cement that can be carried by the needle. In one embodiment, the outside diameter of the injection needle is 13 gauge (0.095" or 2.41 mm) with a 0.077" (1.96 mm) lumen. In some embodiments, the percentage of the inside diameter with respect to the outside diameter of the injection needle is at least about 60%, 65%, 70%, 75%, 80%, 85%, or more.

The steerable injection systems described above are preferably used in conjunction with a mixing and dispensing pump for use with a multi-component cement. In some embodiments, a cement dispensing pump is a hand-held device having an interface such as a tray or chamber for receiving one or more cartridges. In one embodiment, the pump is configured to removably receive a double-barreled cartridge for simultaneously dispensing first and second bone cement components. The system additionally includes a mixing chamber, for mixing the components sufficiently and reproducibly to fully automate the mixing and dispensing process within a closed system.

Bone cement components have conventionally been mixed, such as by hand, e.g., in mixing bowls in the operating room, which can be a time-consuming and unelegant process.

Use of a mixing device such as a double-barreled dispensing pump as disclosed herein is highly advantageous in reducing bone cement preparation time, ensuring that premature cement curing does not occur (i.e., the components are mixed immediately prior to delivery into the body), and ensuring adequate mixing of components.

Two separate chambers contain respective materials to be mixed in a specific ratio. Manual dispensing (e.g., rotating a knob or squeezing a handle) forces both materials into a mixing nozzle, which may be a spiral mixing chamber within or in communication with a nozzle. In the spiral mixing nozzle, all or substantially all mixing preferably occurs prior to the bone cement entering the steerable injection needle and, subsequently, into the vertebra. The cement dispensing hand pump may be attached to the steerable injection needle permanently, or removably via a connector, such as slip-ring Luer fittings. A wide range of dispensing pumps can be modified for use with the present invention, including dispensing pumps described in, for example, U.S. Pat. Nos. 5,184,757, 5,535,922, 6,484,904, and Patent Publication No. 2007/0114248, all of which are incorporated by reference in their entirety.

Figure 13:
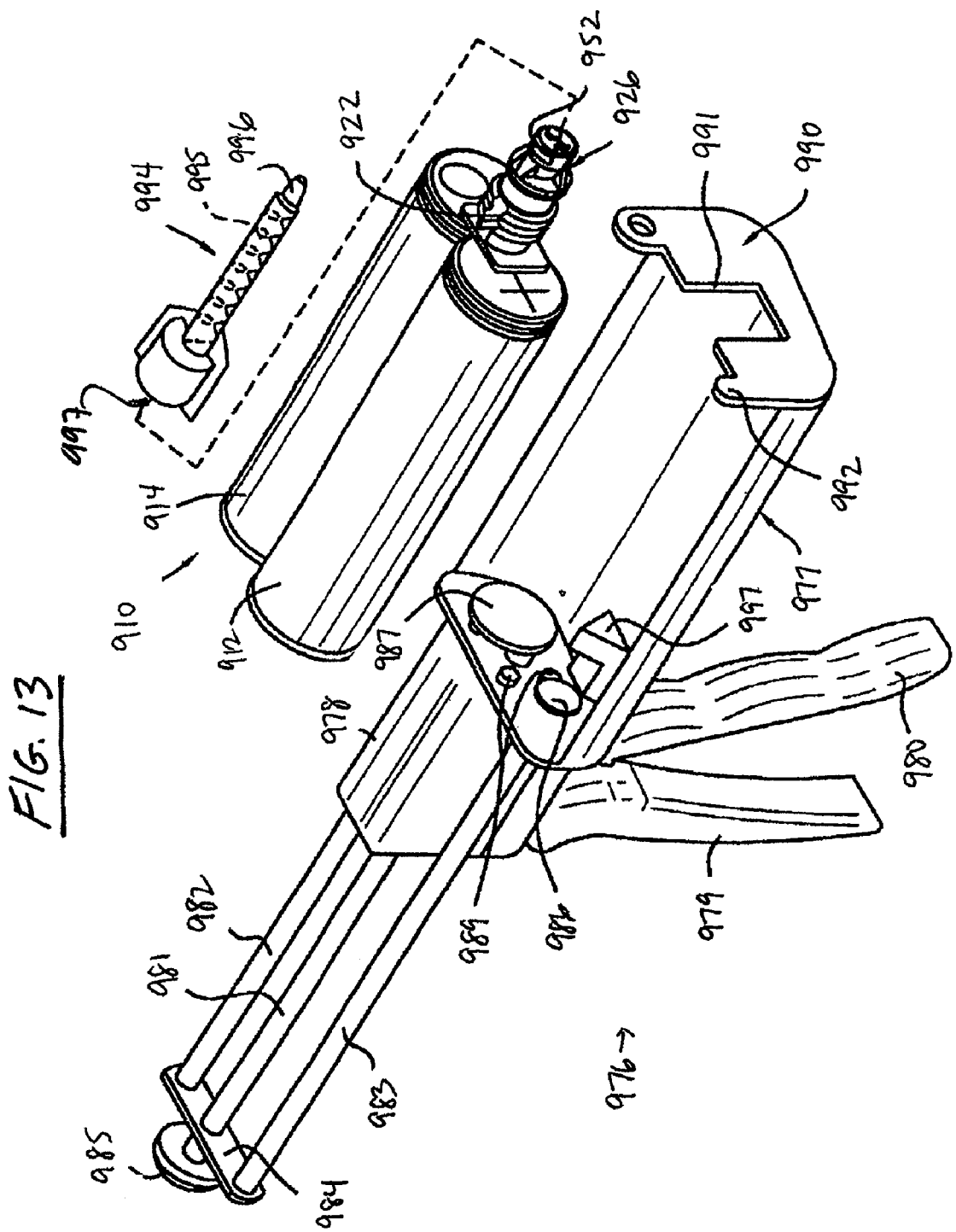
FIG. 13 is a partially exploded schematic view of a cement gun, dual chamber cement cartridge and mixing chamber for use with the present invention.

FIG. 13 illustrates an exploded perspective view of a double-barreled cement dispensing pump, which may be used to practice the present invention. FIG. 13 shows a dispenser gun 976 having a cartridge tray 977 affixed to an actuator 978, for ejecting the compounds contained in a removable, disposable, two-chamber, two-component cartridge 910. The actuator 978 can be any of a variety of mechanisms known in the art, such as found in a caulking gun having either a friction or ratchet advance mechanism. The degree of advancement of the actuator mechanism is controlled by turning a rotatable control such as a wheel or knob (not shown) or by squeezing handles 979, 980, one or both of which moves relative to the other in a conventional manner. In addition to purely mechanical advance mechanisms, the dispensing pump can also be used with a hydraulic, compressed air or electromagnetic advance mechanism. The ejector gun 976 may have at least one actuator rod 981 and may have a piston rod 982, 983 for each cylinder 912, 914, respectively.

The actuator rod 981 and piston rods 982, 983 may be linked at a proximal end such as by a bridge 984 to which a pull knob 985 is attached, such that all rods 981, 982, 983 move simultaneously as an assembly. A piston plate 986 is attached to piston rod 983 at the distal end thereof proximate to the cartridge tray 977. A second piston plate 987 (illustrated as larger than first plate 986) is affixed to the distal end of piston rod 982 and optionally actuator rod 981. In this manner, the ejector gun 976 can be utilized with cartridges having cylinders 912, 914 of the same or different diameters. As depicted in FIG. 13, the cylinders 912, 914 are the same diameter but they could be of different diameters for the purpose of dispensing reactive compounds in other than a 1:1 ratio. In that instance, the larger of the cylinders 912, 914 can be positioned proximate the larger piston plate 987, with the smaller of the cylinders 912, 914 positioned proximate piston plate 986. The pistons 986, 987 could have the same dimensions in other embodiments.

The tray 977 is held to the actuator portion 978 by a plurality of fasteners 989, or by welding, gluing, integral molding or other conventional means. Distal to the actuator 978, the tray has an end plate 990 with a cartridge docking cutout 991 for slideably receiving and embracing the cartridge 910 at the base of the outlet 922.

A cartridge support 997 may extend up from the bottom of the tray 977 and engage the cartridge to retain alignment with the motion of the piston plates 986, 987 to maximize the transfer of force from piston plates 986, 987 to expel the compound from the cartridge 910.

The present disclosure is directed primarily to a cartridge embodiment having two cylindrical chambers. This permits expression of media from the chambers using a plunger arrangement such as a common syringe. However, any of a wide variety of chamber configurations and structures for expressing media from the chamber may be utilized.

Currently favored bone cement compositions are normally stored as two separate components or precursors, for mixing at the clinical site shortly prior to implantation. As has been described above, mixing of the bone cement components has traditionally been accomplished manually, such as by expressing the components into a mixing bowl in or near the operating room. In accordance with the present invention, the bone cement components may be transmitted from their storage and/or shipping containers, into a mixing chamber, and into the patient, all within a closed system. For this purpose, the system of the present invention includes at least one mixing chamber positioned in the flow path between the bone cement component container and the distal opening on the bone cement injection needle. This permits uniform and automated or semi-automated mixing of the bone cement precursors, within a closed system, and thus not exposing any of the components or the mixing process at the clinical site.

Thus, the mixing chamber may be formed as a part of the cartridge, may be positioned downstream from the cartridge, such as in-between the cartridge and the proximal manifold on the injection needle, or within the proximal manifold on the injection needle or the injection needle itself, depending upon the desired performance of the device. The mixing chamber may be a discrete component which may be removably or permanently coupled in series flow communication with the other components of the invention, or may be integrally formed within any of the foregoing components.

In general, the mixing chamber includes an influent flow path for accommodating at least two bone cement components. The first and second incoming flow path are combined, and mixing structures for facilitating mixing of the components are provided. This may include any of a variety of structures, such as a helical flow path, baffles and or additional turbulence inducing structures.

In the embodiment illustrated in FIG. 13, a discrete mixing device 994 includes a proximal connector 997 in fluid flow communication with a distal aperture 996 through a mixing chamber 995. Mixing chamber 995 may include any of a variety of turbulence inducing structures as has been discussed.

The cement mixing gun, cartridge and mixing chamber are illustrated in FIG. 13 in a highly schematic form to assist in understanding the invention. However, as will be appreciated by those of skill in the art, the cement mixing and dispensing systems in accordance with the present invention may be constructed in any of wide variety of forms which may differ significantly in appearance from that illustrated in FIG. 13.

After cement is mixed in mixing nozzle 994, the cement is preferably immediately or eventually directed into the input port 704 of a steerable delivery device, either directly, such as via a Luer lock connector, or through a bridging tubing set.

Cement dispensing pump 976 is preferably configured to accommodate cartridges of appropriate volume for the formation of the amount of bone cement likely to be needed in a single level or a two level vertebroplasty. In some embodiments, cartridges have a volume sufficient to produce a unit volume of mixed bone cement between about 25-200 cc, preferably between 25-100 cc, and in one implementation about 50 cc.

Figure 14:
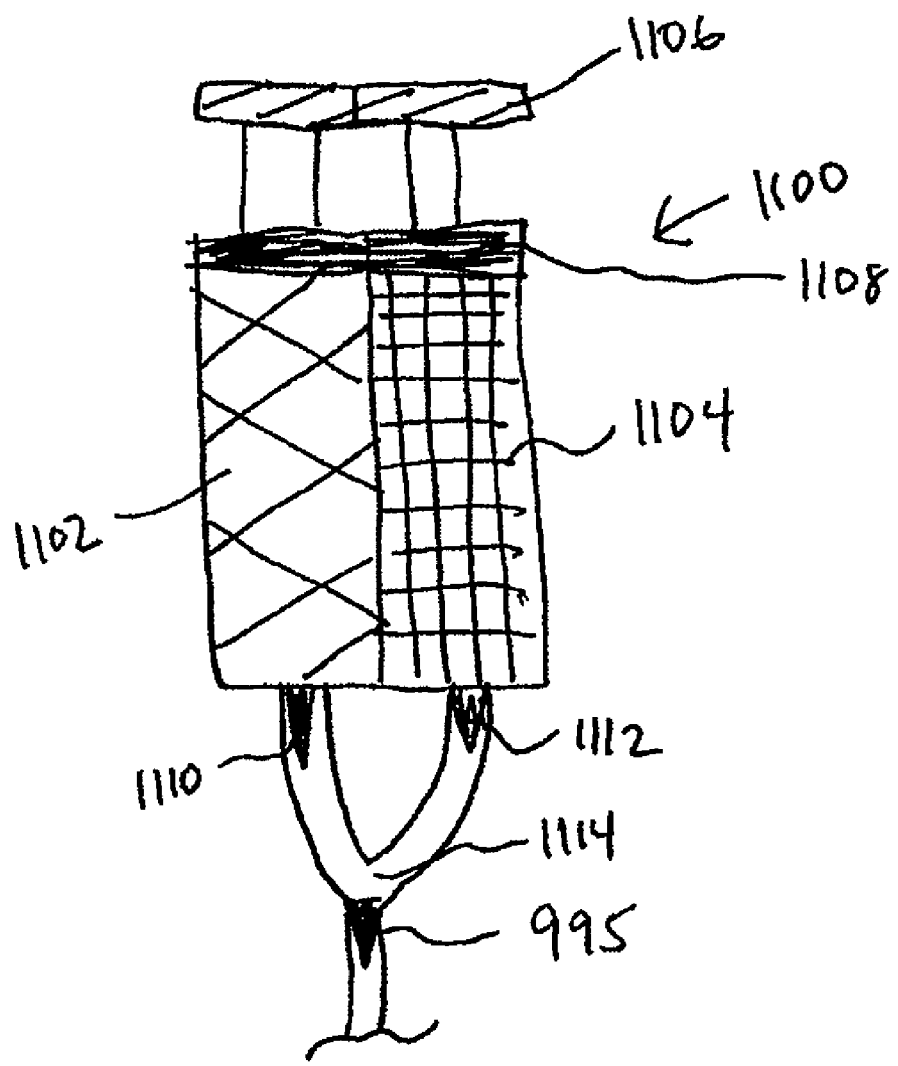
FIG. 14 is a schematic view of an alternate two-part dispensing system for the cement of the present invention.

FIG. 14 illustrates schematically another, simplified embodiment of a bone cement mixing dispenser. Shown are first syringe 1102 and second syringe 1104 filled with first and second bone cement precursor materials respectively (e.g., the contents of cartridges 1A and 1B, or 2A and 2B, respectively and described below). First 1102 and second 1104 syringes may be integrally molded together or coupled together, e.g., by an adhesive and share a common plunger top 1106 such that contents of syringes 1102 and 1104 may be dispensed approximately in a 1:1 or other preset ratio. Applying an axially distally directed force to plunger top 1106 either by hand or by a dispensing device will result in stopper 1108 portions of the plunger to advance distally thereby expressing contents of first 1102 and second 1104 syringes out through nozzles 1110, 1112 and into Y-connector tubing 114 into mixing nozzle 995, and thereafter into the input port 704 of a steerable delivery device.

In some embodiments, a bone cement composite is packaged in two separate chambers contained in a single cartridge. This may be useful, for example, for delivering conventional two part PMMA formulations in an otherwise conventional vertebroplasty or kyphoplasty procedure.

In other embodiments, the system is adapted for delivering a bone cement composite in which the final construct comprises a mass of hardened cement having a particulate content with a non uniform spatial distribution. In this embodiment, a total of three or four chambers will normally be used which may conveniently be distributed into two chambers each in two cartridges.

Tables 1-2 below depict the contents and concentrations of one exemplary embodiment of bone cement precursors. Chambers 1A and 1B contain precursors for a first cement composition for distribution around the periphery of the formed in place vertebral body implant with a higher particle concentration to promote osteoinduction, as discussed previously in the application. Chambers 2A and 2B contain precursors for a second cement composition for expression more centrally within the implanted mass within the vertebral body, for stability and crack arresting, as discussed previously in the application.

One of ordinary skill in the art will recognize that a wide variety of chamber or cartridge configurations, and bone cements, can be used with the present injection system. For example, in one embodiment, a first cartridge includes pre-polymerized PMMA and a polymerization catalyst, while a second cartridge includes a liquid monomer of MMA as is common with some conventional bone cement formulations.

In some embodiments, the contents of two cartridges can be combined into a single cartridge having multiple (e.g., four) chambers. Chambers may be separated by a frangible membrane (e.g., 1A and 2A in a first cartridge and 1B and 2B in a second cartridge, each component separated by the frangible membrane or other pierceable or removable barrier). In other embodiments, contents of the below cartridges can be manually pre-mixed and loaded into the input port of the injection system without the use of a cement mixing dispenser.

TABLE 1

| Chamber 1A | |
|---|---|
| Methyl methacrylate (balance) | Hydroquinone (~75 ppm) (stabilizer) |
| N,N-dimethyl-p-toluidine (~0.9%) (catalyst for polymerization) | Sterile bone particles (≧35 wt. %) |
| Barium sulfate (~20 wt. %) (radio-opacifier) | |

TABLE 1-continued

| Chamber 1B | |
|---|---|
| Benzoyl peroxide (~2%) (activator for polymerization) | Physiological saline or poppy seed oil (balance) |

TABLE 2

| Chamber 2A | |
|---|---|
| Methyl methacrylate (balance) | Hydroquinone (~75 ppm) (stabilizer) |
| N,N-dimethyl-p-toluidine (~0.9%) (catalyst for polymerization) | Sterile bone particles (~30 wt. %) |
| Barium sulfate (~20 wt. %) (radio-opacifier) | |
| Chamber 2B | |
| Benzoyl peroxide (~2%) (activator for polymerization) | Physiological saline or poppy seed oil (balance) |

Figure 15A:
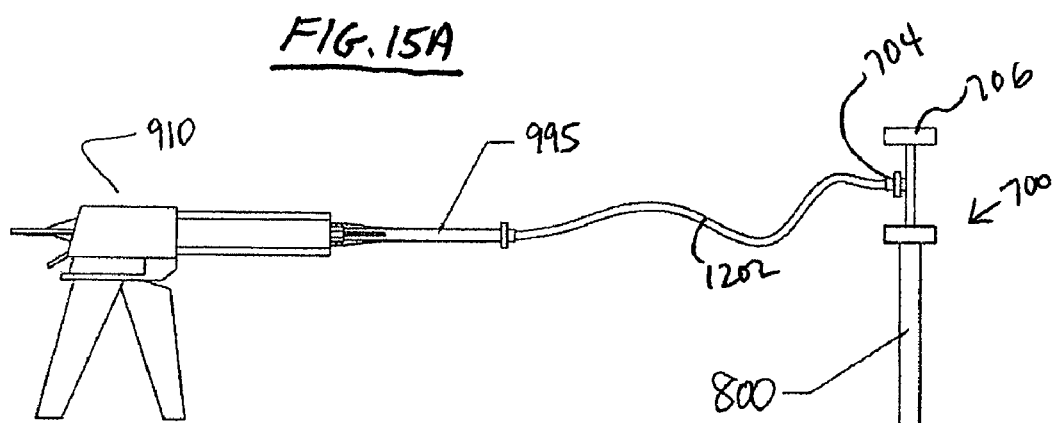
FIGS. 15A and 15B are schematic views of a bone cement delivery system in accordance with the present invention.
Figure 15B:
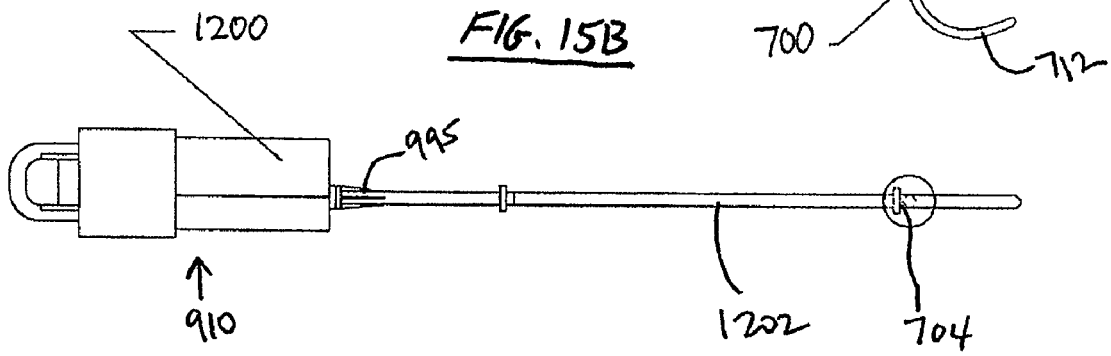

As illustrated in FIGS. 15A-B, in one embodiment, a system or kit for implanting bone cement includes at least some of the following components: a stylet configured to perforate a hole into the pedicle of the vertebral body; an introducer cannula 800 for providing an access pathway to the treatment site, a steerable injection needle 700 to deliver bone cement to a desired location, and, a cement dispensing pump 910 preferably configured to accommodate one or two or more dual chamber cartridges 1200 as well as a mixing nozzle 995.

The stylet may have a diameter of between about 0.030" to 0.300", 0.050" to about 0.200" and preferably about 0.100" in some embodiments. The introducer cannula 800 is between about 8-14 gauge, preferably between about 10-12 gauge, more preferably 11 gauge in some embodiments. The introducer cannula 800, which may be made of any appropriate material, such as stainless steel (e.g., 304 stainless steel) may have a maximum working length of no more than about 12", 8", or 6" in some embodiments. One or two or more bone cement cartridges, each having one or two or more chambers, may also be provided. Various other details of the components have been described above in the application.

One embodiment of a method for delivering bone cement into a vertebral body is now described, and illustrated in FIGS. 16A-F. The method involves the general concept of vertebroplasty and kyphoplasty in which a collapsed or weakened vertebra is stabilized by injecting bone cement into cancellous bone.

Figure 16A:
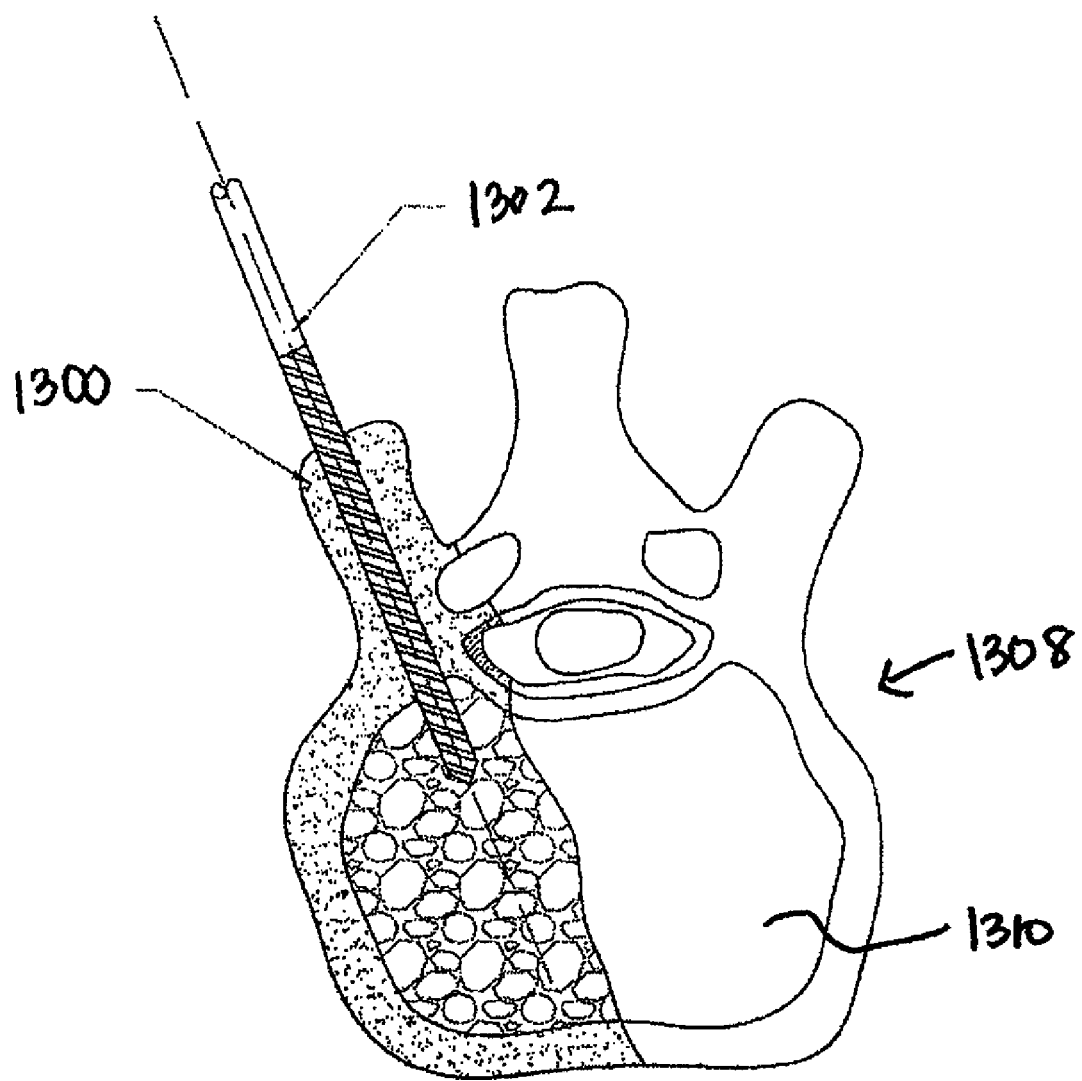
FIGS. 16A through 16F show stages in the method of accomplishing vertebroplasty in accordance with present invention.
Figure 16B:
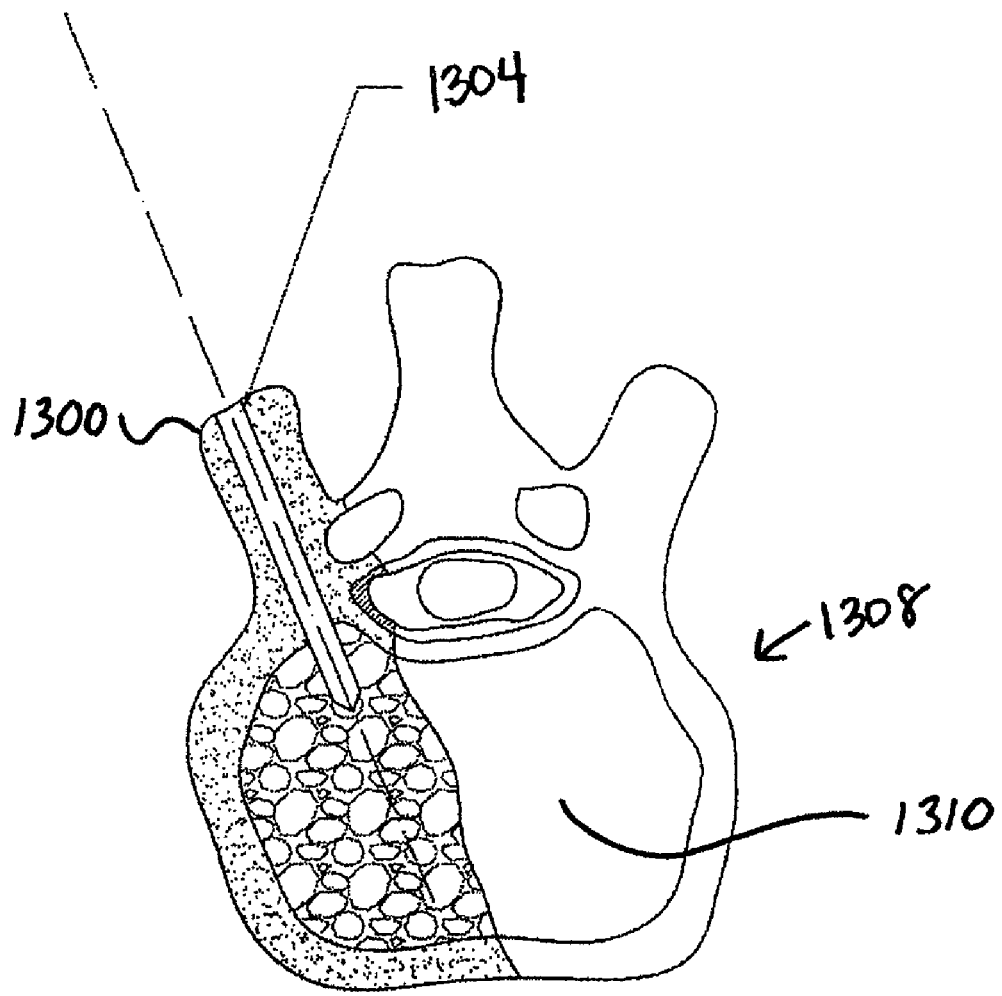
Figure 16C:
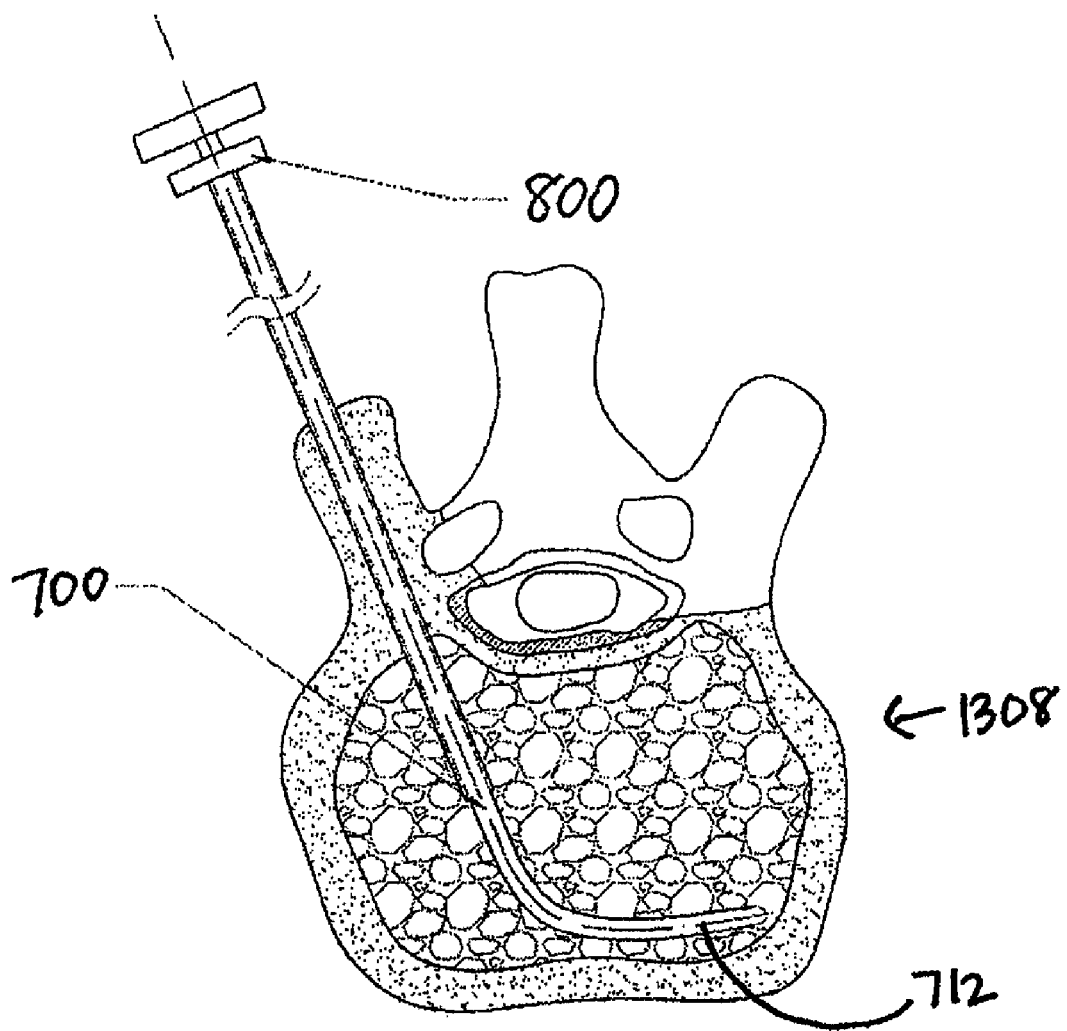

The cement implantation procedure is designed for uni-transpedicular access and generally requires either a local anesthetic or short-duration general anesthetic for minimally invasive surgery. Once the area of the spine is anesthetized, as shown in FIGS. 16A-B, the physician inserts a stylet 1302 to perforate a lumen 1304 into the pedicle wall 1300 of the vertebra 1308 to gain access to the interior of the vertebral body 1310. As illustrated in FIG. 16C, the introducer cannula 800 is then inserted through the lumen 1304 for bone access as well as acting as the guide for the steerable injection needle 700. The introducer cannula 800 is sized to allow physicians to perform vertebroplasty or kyphoplasty on vertebrae with small pedicles 1300 such as the thoracic vertebra (e.g., T5) as well as larger vertebrae. In addition, this system and method is advantageously designed to allow uni-transpedicular access as opposed to bi-pedicular access, resulting in a less invasive surgical procedure.

Once bone access has been achieved, as shown in FIG. 16C the steerable injection needle 700 such as any of the devices described above can be inserted through the introducer cannula 800 and into the vertebra 1308. The entire interior 1310 of the target vertebral body may be accessed using the steerable injection needle 800. The distal end 712 of the needle 700 can be laterally deflected, rotated, and/or proximally retracted or distally advanced to position the bone cement effluent port at any desired site as previously described in the application. The radius can be adjusted by means of an adjustment control, such as a knob on the proximal end of the device as previously described.

Figure 16D:
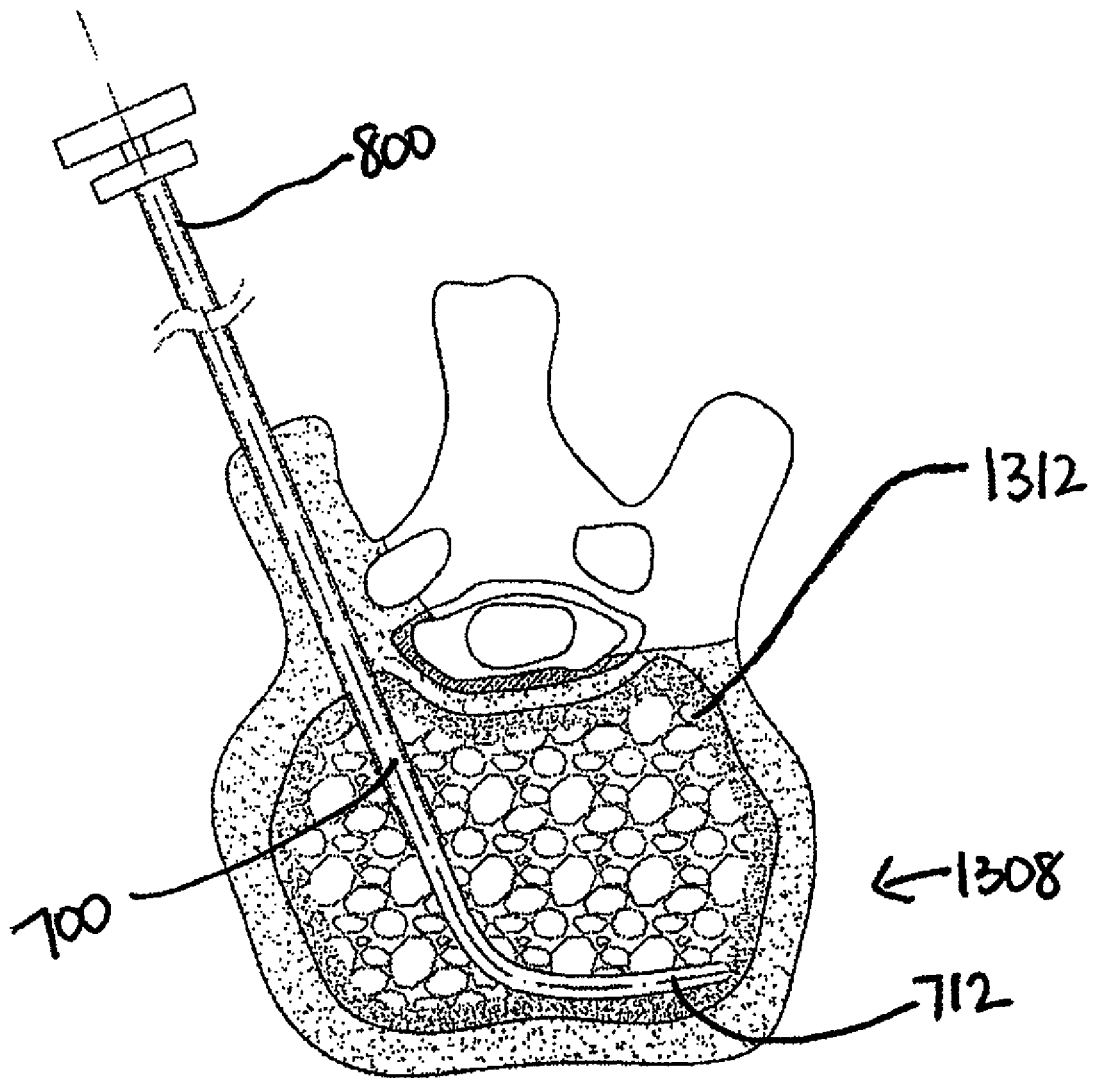
Figure 16E:
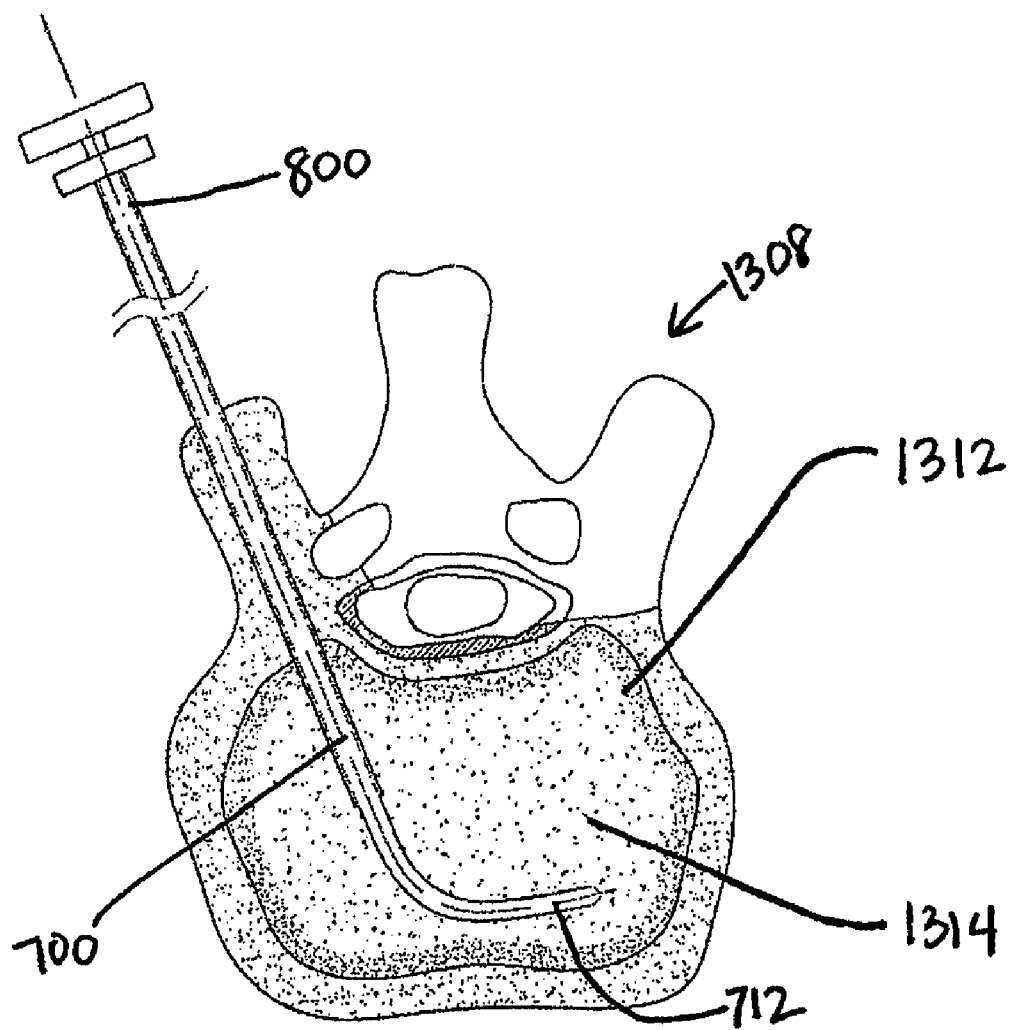

The actual injection procedure may utilize either one or two basic steps. In a one step procedure, a homogenous bone cement is introduced as is done in conventional vertebroplasty. The first step in the two step injection involves injection of a small quantity of PMMA with more than about 35%, e.g., 60% particles such as inorganic bone particles onto the periphery of the treatment site, i.e., next to the cortical bone of the vertebral body as shown in FIG. 16D. This first cement composite 1312 begins to harden rather quickly, forming a firm but still pliable shell, which is intended to minimize or prevent any bone marrow/PMMA content from being ejected through any venules or micro-fractures in the vertebral body wall. The second step in the procedure involves an injection of a bolus of a second formulation of PMMA with a smaller concentration such as approximately 30% inorganic bone particles (second cement composite 1314) to stabilize the remainder of the weakened, compressed cancellous bone, as illustrated in FIG. 16E.

Figure 16F:
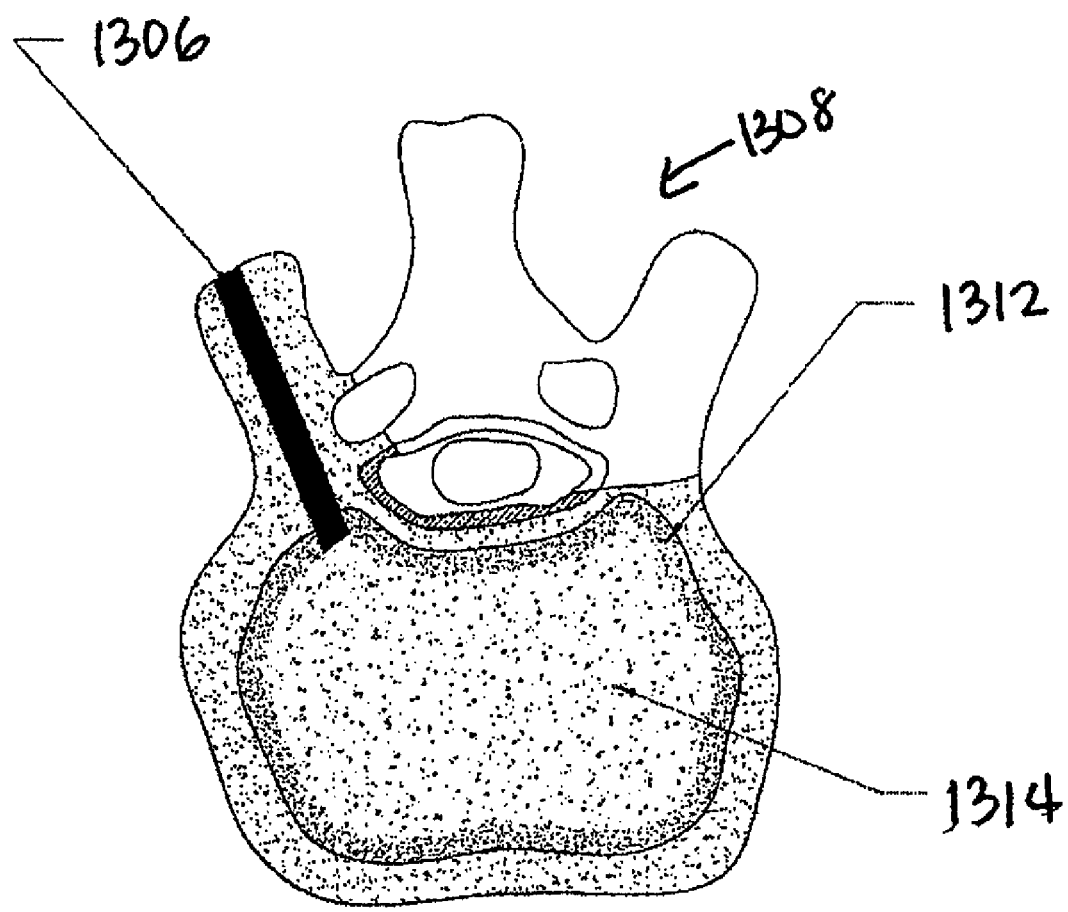

Injection control for the first and second steps is provided by an approximately 2 mm inside diameter flexible introducer cannula 800 coupled to a bone cement injection pump (not shown) that is preferably hand-operated. Two separate cartridges containing respective bone cement and inorganic bone particle concentrations that are mixed in the 60% and 30% ratios are utilized to control inorganic bone particle to PMMA concentrations. The amount of the injectate is under the direct control of the surgeon or interventional radiologist by fluoroscopic observation. The introducer cannula 800 is slowly withdrawn from the cancellous space as the bolus begins to harden, thus preventing bone marrow/PMMA content from exiting the vertebral body 1308. The procedure concludes with the surgical incision being closed, for example, with bone void filler 1306 as shown in FIG. 16F. Both the high and low bone cement particle concentration cement composites 1312, 1314 harden after several minutes. In vitro and in vivo studies have shown that the 60% bone-particle impregnated bone cement hardens in 2-3 minutes and 30% bone-particle impregnated bone cement hardens between 4 to 10 minutes.

The aforementioned bone cement implant procedure process eliminates the need for the external mixing of PMMA powder with MMA monomer. This mixing process sometimes entraps air in the dough, thus creating porosity in the hardened PMMA in the cancellous bone area. These pores weaken the PMMA. Direct mixing and hardening of the PMMA using an implant procedure such as the above eliminates this porosity since no air is entrapped in the injectate. This, too, eliminates further weakening, loosening, or migration of the PMMA.

While described herein primarily in the context of vertebroplasty, one of ordinary skill in the art will appreciate that the disclosed injection system can be used or modified in a wide range of clinical applications, such as, for example, other orthopedic applications such as kyphoplasty, treatment of any other bones, pulmonary, cardiovascular, gastrointestinal, gynecological, or genitourinary applications. While this invention has been particularly shown and described with references to embodiments thereof, it will be understood by those skilled in the art that various changes in form and details may be made therein without departing from the scope of the invention. For all of the embodiments described above, the steps of the methods need not be performed sequentially and the individual components of the devices may be combined permanently or be designed for removable attachment at the clinical site.

What is claimed is:

1. A system for performing vertebroplasty, comprising:
a steerable injection needle configured for one hand operation including an elongate shaft having a proximal portion having a proximal end and a deflectable distal portion having a proximal end distal end, and an opening from which bone cement can exit from the distal portion, wherein the elongate shaft further comprises a first longitudinal axis extending from the proximal end of the proximal portion to the proximal end of the deflectable distal portion, the steerable injection needle further comprising an input port having a second longitudinal axis spaced apart from and at an angle with respect to the first longitudinal axis of the steerable injection needle for receiving bone cement from a cement dispensing pump, wherein the elongate shaft from the proximal end of the deflectable distal portion to the distal end is movable from a first substantially straight configuration to a second configuration not substantially coaxial with the proximal portion, wherein the steerable injection needle further comprises an adjustment control configured to move the distal portion of the elongate shaft from the first configuration to the second configuration, the adjustment control located proximal on the injection needle relative to the input port;
a cement dispensing pump configured to house a first bone cement component and a second bone cement component; and
a mixing nozzle for mixing the first bone cement component and the second bone cement component into a bone cement composite.

2. The system of claim 1, further comprising a stylet for creating an access pathway in a pedicle.

3. The system of claim 1, further comprising an introducer cannula.

4. The system of claim 1, further comprising the first bone cement component, wherein the first bone cement component comprises MMA.

5. The system of claim 4, further comprising the second bone cement component.

6. The system of claim 4, further comprising the second bone cement component, wherein the second bone cement component comprises at least about 35% weight percent of bone particles.

7. The system of claim 1, wherein the input port comprises a Luer lock.

8. The system of claim 1, wherein the steerable injection needle comprises an end cap on the distal end of the deflectable distal portion of the elongate shaft.

9. The system of claim 1, wherein the steerable injection needle comprises a pull wire operably connected to the distal end of the deflectable distal portion of the elongate shaft.

10. The system of claim 1, wherein the steerable injection needle comprises a filter operably connected to a distal opening of the deflectable distal portion of the elongate shaft.

11. The system of claim 1, wherein the distal portion of the elongate shaft has a working length of at least about 20% of the total working length of the needle.

12. The system of claim 1, wherein the steerable injection needle comprises a spring coil.

13. The system of claim 1, wherein the deflectable distal portion of the elongate shaft is movable from a first substantially straight configuration in an unstressed state to a second deflected configuration.

* * * * *

UNITED STATES PATENT AND TRADEMARK OFFICE
CERTIFICATE OF CORRECTION

PATENT NO.        : 7,842,041 B2                                     Page 1 of 1
APPLICATION NO.   : 12/261987
DATED             : November 30, 2010
INVENTOR(S)       : Liu et al.

It is certified that error appears in the above-identified patent and that said Letters Patent is hereby corrected as shown below:

Column 1, Line 19, Change "(http)" to --(http--.

Column 11, Line 7, Change "crisscrossing" to --cris-crossing--.

Column 20, Line 21, claim 1, Change "proximal end" to --proximal end, a--.

Signed and Sealed this
Twenty-fifth Day of October, 2011

David J. Kappos
*Director of the United States Patent and Trademark Office*